US009833437B2

(12) United States Patent
Saikh et al.

(10) Patent No.: US 9,833,437 B2
(45) Date of Patent: Dec. 5, 2017

(54) SMALL MOLECULE INHIBITOR OF MYD88 FOR THERAPEUTIC TREATMENT AGAINST ALPHAVIRUS AND STAPHYLOCOCCAL ENTEROTOXIN INFECTIONS AND TOXIN EXPOSURE

(71) Applicant: The United States of America, as Represented by the Secretary of the Army, Washington, DC (US)

(72) Inventors: Kamal U Saikh, Derwood, MD (US); Julius M. Rebek, Jr., La Jolla, CA (US); Pamela J Glass, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/369,004

(22) Filed: Dec. 5, 2016

(65) Prior Publication Data
US 2017/0079952 A1 Mar. 23, 2017

Related U.S. Application Data

(63) Continuation of application No. PCT/US2015/000068, filed on Jun. 5, 2015.

(60) Provisional application No. 62/010,628, filed on Jun. 11, 2014.

(51) Int. Cl.
C07D 403/12 (2006.01)
A61K 31/4025 (2006.01)
C07D 295/185 (2006.01)

(52) U.S. Cl.
CPC ...... *A61K 31/4025* (2013.01); *C07D 295/185* (2013.01); *C07D 403/12* (2013.01)

(58) Field of Classification Search
CPC .......................... A61K 31/4025; C07D 403/12
See application file for complete search history.

(56) References Cited

FOREIGN PATENT DOCUMENTS

WO   WO 2010-011325   1/2010
     A-2

OTHER PUBLICATIONS

Cannon ("Analog Design" in Burger's Medicinal Chemistry and Drug Discovery, 6th ed. 2003, Wiley, pp. 687-714).*
Atkins ("The Pathogenesis of Alphaviruses", ISRN Virology, 2013, p. 1-22).*
Siednienko et al. (J Immunol 2011; 186:2514-2522).*
Kissner et al. (The Journal of Biological Chemistry, 2011, v. 286, p. 31385-31396).*
Weighardt et al. (J Immunol 2002; 169:2823-2827).*
Davis, et al., MyD88-dependent and independent signaling . . . , Proceedings of the National Academy of Sciences of the USA, 2006, vol. 103, No. 8, pp. 2953-2958.
Kissner, et al., Therapeutic inhibition of pro inflammatory signaling and toxicity . . . , PLoS ONE, 2012, vol. 7, No. 7, e40773, internal pages 1-12.
Loiarro, et al., Pivital Advance: inhibition of MyD88 dimerization and recruitment . . . , J. of leukocyte biology, 2007, vol. 82, No. 4, pp. 801-810.
Alam et al., Structure-based Design and Synthesis of a Small Molecule that Exhibits Anti-inflammatory . . . , Chemical biology & drug design [Epub.] 2014, vol. 86, No. 2, p. 200-209.
Richter, et al., Predictive compound accumulation rules yield a broad-sprectrum antiotic, Nature, vol. 545, p. 299-307.
Fitzgerald, et al, IKKE and TBKI are essential components of the IRF3 sinnaling pathway (2003)Nature Immunology, vol. 4, No. 5, pp. 491-496.
Griflin, Immune Responses to RNA-Virus Infections of the CNS, (2003), Nat. Reviews, vol. 3, pp. 493-503.
Liu, et al., Intracellular MHC class II molecules promote TLR-triggered innate immune responses by maintaining activiation of the kinase Btk, (2011), Nat Imm v12 #5, p. 416-425.
Taniguchi, et al., IRF Family of Transcription Factors as Regulatos of Host Defence, (2001), Ann. Rev. Immunol. vol. 19, 623-655.
Honda, IRFs: master regulators of signalling by Toll-like receptors . . . , (2006), Nature Review, vol. 6, pp. 644-658.
Sun, et al., MyD88-mediated stabilization of interferon-y-induced cytokine and chemokine mRNA, (2006)Nat. Immunol., vol. 7, No. 4, pp. 375-381.

(Continued)

*Primary Examiner* — Robert Havlin
(74) *Attorney, Agent, or Firm* — Elizabeth Arwine

(57) ABSTRACT

A synthetic molecule 4210 and a therapeutic use of a synthetic small molecule 4210 for treating viral infections, especially encephalitic alphavirus infections. The compound 4210 showed antiviral efficacy by up regulation type 1 interferon (IFN) specifically IFN-β. The compound 4210 was designed and synthesized by a structure-based approach targeting intracellular adaptor protein, myeloid differentiation primary response protein 88 (MyD88). Besides having an antiviral effect, the compound 4210 also demonstrated therapeutic efficacy for treating inflammatory syndrome associated with Gram positive bacterial infections such as exposure to staphylococcal enterotoxin B (SEB) induced toxic shock syndrome (TSS) in mice and can potentially be used in clinical set up for treating sepsis and septic shock. In addition, the application of molecule 4210 can treat sepsis and septic shock triggered by exposure to other biological agents such as *Francisella tularensis* or *Burkholderia mallei* known to cause tularemia and glanders, respectively. The molecule 4210 has the potential for a broad-spectrum therapeutic use.

20 Claims, 37 Drawing Sheets

(56) References Cited

OTHER PUBLICATIONS

Cook, et al., Toll-like receptors in the pathogenesis of human disease (2004), Nat. Immunology, vol. 5, No. 10, pp. 974-979.
Takeda et all, Toll-Like Receptors, (2003), Annu. Rev. Immunol., 21:335-76.
Theofilopoulos, et al. Type I Interferons (a/B) In Immuity and Autoimmunity, (2005), Annu. rev. Immunol. 23:307-36.
Hassan, et al. An unexpected role of MHC class, (2011), Nat. Immun. vol. 12, No. 5, pp. 375-376.
Aikira, et al., Toll-Like Receptor Signalling (2004), Nat. Reviews Immunology, vol. 4, pp. 499-511.
Barton, et al., Toll-Like Receptor Signaling Pathways, (2003), Science, vol. 300, pp. 1524-1525.
Ojaniemi, Phosphatidlyinositol 3-kinase is involved in Toll-like receptor . . . , (2003), Eur.J. Immunol, 33: 597-605.
Jeffereies, et al., Bruton's Tyrosine Kinase . . . , (2003) J.Biol. Chem, vol. 278, No. 28, pp. 26258-26264.
Honda, et al., Roll of a transductional transcriptional . . . , (2004), PNAS, vol. 101, No. 43, pp. 15416-16421.
Kissner, Activation of MyD88 Signaling upon Staphyloccal . . . , (2011), PLos One, vol. 6, Issue 1.
Harton. et al., The Cytoplasmic and Transmembrane Domains of MHC . . . , (1995), Immunity, vol. 3, pp. 349-358.
Frei, et al., MHC Class Molecules Enhance Toll-Like . . . , (2010), PLos One, vol. 5, issue 1.
Stiles, et al., Toxicity of Staphylococcal Entertoxins..(1993), Infection&Immun., vol. 61, No. 12, pp. 5333-5338.
Waag, et al., Cwell-Mediated and Humoral Immune Responses . . . , (1995), Clinical and Diag. Lab. Imm. vol. 2, No. 2, pp. 143-148.
Kissner, et al., A small Molecule That mimics the BB-loop. . . , (2011), Jour of Biological chem, vol. 286, No. 36, pp. 31385-31396.
Kissner, et al., Therapeutic Inhibition of Pro-Inflammatory Signaling . . . , (2012), PLOS One, vol. 7, issue 7.
Davis, et al., MyD88-dependent and independent signaling . . . , (2006), PNAS, vol. 103, No. 8, pp. 2953-2958.
Kissner, et al., Staphyloccal enterotoxin A induction of Pro-inflammatory cytokines, (2010) Immunology, vol. 130, p. 516-526.
Harton, et al., Length and Sequence Requirements of the Cytoplasmic Domain . . . (1993), J. of Immunology, vol. 151, No. 10, pp. 5282-5289.
Mrkic, et al., Lymphatic Dissemination and comparative Pathology of . . . , (2000), J. of Virology, bol. 74, No. 3, pp. 1364-1372.
Leib, et al., Interferons regulate the Phenotype of Wild-type . . . , (1999), J. Exp. Med., vol. 189, No. 4, pp. 663-672.
Noisakran, et al., Extopic Expression of DNA Encoding IFN-a1 in the Cornea . . . , (1999), J. of Immun., vol. 162, pp. 4184-4190.
Garcia-Sastre, et al., The Role of Interferon in Influenze Virus . . . , (1998), J. of Virology, vol. 72, No. 11, pp. 8550-8558.
Yeow, Antiviral Actibities of Individual Murine IFN-a Subtupes . . . , (1998), J. Immunol., vol. 160, pp. 2932-2939.
Ryman, et al., Alpha/Beta Interferon Protects Adult Mice from Fatal Sindbis . . . , (2000), J. Virology, vol. 74, No. 7, pp. 3366-3378.
Van Den Broek, et al., Immune Defence in Mice Lacking Type I . . . (1995), Immunol. Reviews, No. 148, p. 5-18.
Mamane, et al., Interferon Regulatory factors: the next generation, (1999), Gene 237, pp. 1-14.
Nguyen, et al., The growing Family of Interferon Regulatory Factors, (1997), Cytokine&Growth Factor Rev., vol. 8, No. 4, pp. 293-312.
Durbin, et al., Targeted Disruption of the Mouse Stat1 Gene . . . , (1996), Cell, vol. 84, pp. 443-450.
Spotts, et al., Resistance to Alpha/Beta Interferons Correlates with the Epizootic and virulence Potential . . . , (1998), J. Virology, vol. 72, No. 12, pp. 10286-10291.
Aguilar, et al., Structural and Nonstructural Protein Genome Regions . . . (2008), J. Virology, vol. 82, No. 10, pp. 4920-4930.
Deonarian, et al., Impaired Antiviral Response and Alpha/Beta Interferon . . . , (2000), J. Virology, vol. 74, No. 7, pp. 3404-3409.

Fitzgerald, et al., LPS-TLR4 Signaling to IRF-3/7 . . . , (2003), J. Exp. Med, vol. 198, No. 7, pp. 1043-1055.
Honda, et al., Regulation of the Type I IFN induction . . . , (2005), Intern. Immun. vol. 17, No. 11, pp. 1367-1378.
Barnes, et al., Virus-specific Activation of a Novel Interferon . . . , (2001), J of Biolog. Chem., vol. 276, No. 26, pp. 23382-23390.
Miyamoto, et al., Regulated Expression of a Gene Encoding a Nuclear Factor, IRF-1 . . . (1988), Cell, vol. 54,, pp. 903-913.
LeBon, et al., Links between innate and adaptive immunity . . . , (2002) Current Opinion in Imm., 14:432-436.
Alam, et al., Structure Based Design and Synthesis of a small molecule . . . , (2015), Chem Biol. Drug Des, vol. 86, pp. 200-2009.
Negishi, et al., Beneficial innate signaling interference for antibacterial responses . . . , (2013), PNAS, vol. 110, No. 49, 19884-19889.
Ayithan, et al., Ebola Virus-Like Particles Stimulate Type I Interfereons . . . , (2014), J. of Interferons&Cytokine Res, vol. 34, No. 2, pp. 79-89.
Fuse, et all, Myeloid Differentiation Factor-88 Plays a crucial . . . , (2005), Circulation, 112, pp. 2276-2285.
Iliev, et al., MyD88 interacts with Interferon Regulation Factor . . . , (2011) J. Biol. Chem. vol. 286, No. 49, pp. 427715-427724.
Siednieko, et al., Absence of MyD88 Results in Enhances . . . , (2011), J. Immunol, 186:2514-2522.
Siednienko, et al., TLR30-mediated IFN-B gene . . . , (2010), Eur. J. Immun. 40:3150-3160.
Johnson, et all, MyD88 Functions as a Negative Regulator . . . , (2008), J. Biol. Chem., vol. 283, No. 7, pp. 3988-3996.
Kenny, et al., MyD88 Adaptor-Like is Not Essential for TLR2 . . . , (2009), J. Immunoo. 183:3642-3651.
Hemmi, et al., The Roles of Two IkB Kinase-related Kinases . . . (2004), J. Exp. Med, vol. 199, No. 12, pp. 1641-1650.
Kawai, et al., Lipopolysaccharide Stimulates teh MyD88-Independent Pathway . . . , (2001), J Immunol, vol. 167, pp. 5887-5894.
Alam, et al., Structure-Based Design and Synthesis of a small Molecule . . . , (2015) Chem Biol. Drug Des. 86:200-2009.
Servant, et al., Multiple signaling pathways leading to the activation . . . , (2002), Biochem Pharm., vo. 64, pp. 985-992.
Lin, et al., Virus-Dependent Phosphorylaton of the IRF-3 . . . , (1998), Mol. and Cell. Biol., vol. 18, No. 5, pp. 2986-2996.
Wathelet, et al., Virus Infection Induces the Assembly of Coordinately . . . (1998), Molec, Cell., vol. 1, pp. 507-518.
Sharma, et al., Oligonucleotide array analysis of Toll-like . . . , (2009), J. General Virol, vol. 90, pp. 1836-1847.
Akira et al., Functios of Toll-like receptors . . . (2004)C.R. Biologies vol. 327, pp. 581-589.
Hoshino, et al., Differential involvement of IFN-B in Toll-like receptor . . . , (2002), Internat. Immun. vol. 14, No. 10, pp. 1225-1231.
Grieder, et al., Role of Interferon and Interferon Regulatory . . . (1999) Virology, vol. 257, pp. 106-118.
Greider, at al., Specific Restrictions in the Progression of Venezuelan . . . (1995), Virology, No. 206, pp. 994-1006.
Dupuy, et al., Directed molecular evolution improves the Immunogenicity . . . , (2009), Vaccine 27, pp. 4152-4160.
Steele, et al., Pathology of Animal Models of Alphavirus Encephalitis, (2010), Veterinary Pathology, 47(5) 790-805.
Griffin, Immune responses to RNA-Virus Infections of the CNS, (2003), Nature Review/Immunol., vol. 3, pp. 493-502.
Detje, et al., Local Type I IFN Receptor Signaling Protects . . . , (2009), J Immunol., 182:2297-2304.
Daffis, et al., Cell-specific IRF-3 Responses . . . , (2007), PLOS Pathogens vol. 3 , issue 7, e106.
Sato, et al., Involvement of teh IRF family transcription . . . , (1998), FEBS Letters vol. 425, pp. 112-116.
Servant, at al. Indentification of the Minimal Phosphoacceptor Site . . . , (2003), J. of Biol. Chem., vol. 278, pp. 9441-9447.
Baron, et al., The Interferons Mechanisms of Action . . . , (1991), JAMA, vol. 266, No. 10, pp. 1375-1383.
Simmons, et al., Venezuelan Equine Encephalitis Virus Disrupts STAT1, (2009), J. Voirology, vol. 83, No. 20, pp. 10571-10581.
O'Neill, (2003) The role of MyD88-like adapters in Toll-like receptor signal transductions, Biochem Soc. Trans.; 31: 643-647.

(56) References Cited

OTHER PUBLICATIONS

Kiesner, etal., (2010) MyD88-dependent pro-inflammatory cytokine response contributes to lethal toxicity of staphylococcal enterotoxin B in mice., Innate Immun; 14(5) 451-462.

* cited by examiner

SMALL MOLECULE INHIBITOR OF MYD88 FOR THERAPEUTIC TREATMENT AGAINST ALPHAVIRUS AND STAPHYLOCOCCAL ENTEROTOXIN INFECTIONS AND TOXIN EXPOSURE

This application claims priority and is a continuation of PCT/2015/000068 filed Jun. 5, 2015, pending, which claims priority of U.S. provisional application Ser. No. 62/010,628 filed Jun.11, 2014.

GOVERNMENT INTEREST

The invention described herein may be manufactured, used and licensed by or for the U.S. Government.

BACKGROUND OF THE INVENTION

Field of the Invention

This invention is in the field of therapeutic use against virus infection especially New World alphaviruses such as Venezuelan equine encephalitis virus (VEEV) and other alphavirus infections (EEEV and WEEV (Category B select agents). These alpha viruses represent a significant public health threat as both emerging infectious diseases and potential bio-terror agents due to their morbidity and mortality in humans, high infectivity in aerosols ease of production and considerable stability. This invention also relates to the field of immunization for gram positive bacterial infections, especially for treating staphylococcal enterotoxins (SE) intoxication.

Description of Related Art

There are currently no FDA-licensed vaccines or therapeutics to prevent or treat alphavirus infections in humans. There is a need for a host directed anti-viral therapy approach. Also to date, there is no small molecule therapeutics available for SEB exposure therapy.

SUMMARY OF THE INVENTION

The invention described herein provides a therapeutic use of a synthetic small molecule 4210 for treating viral infections, especially encephalitic alphavirus infections. The compound 4210 showed antiviral efficacy by up regulation type 1 interferon (IFN) Specifically IFN-β. The compound 4210 was designed and synthesized by a structure-based approach targeting adaptor protein, myeloid differentiation primary response protein 88 (MyD88). Besides having an antiviral effect, the compound 4210 also demonstrated therapeutic efficacy for treating inflammatory syndrome associated with Gram positive bacterial infections such as exposure to staphylococcal enterotoxin B (SEB) induced toxic shock syndrome (TSS) in mice and can potentially be used in clinical set up for treating sepsis and septic shock. In addition, the application of molecule 4210 can treat sepsis and septic shock triggered by exposure to other biological agents such as *Francisella tularensis* or *Burkholderia mallei* known to cause tularemia and glanders, respectively. The molecule 4210 has the potential for a broad-spectrum therapeutic use.

BRIEF DESCRIPTION OF THE FIGURES

FIG. 2D is a series of graphs showing dose dependent inhibition of pro-inflammatory cytokine production by compound 4210 in primary PBMC culture stimulated with LPS (*F. tularensis* or *E. coli*) or irradiated *B. mallei*;
FIG. 3A is a graph showing MyD88-specific signaling inhibited by compound 4210; data being presented as $IC_{50}$.

DETAILED DESCRIPTION

Figure 1A:
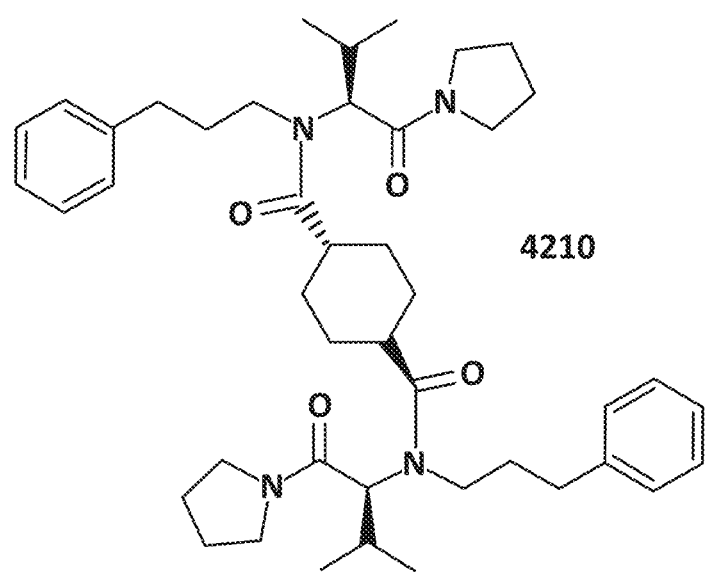
FIG. 1A is the chemical structure of molecule 4210.

Reference will now be made in detail to embodiments of the present invention, examples of which are illustrated in the accompanying drawings, wherein like reference numerals refer to the like elements throughout. The embodiments are described below to explain the present invention by referring to the figures.

The invention described herein provides a small molecule and a therapeutic use of a synthetic small molecule 4210 (Mol. Wt. 713) for treating staphylococcal enterotoxin intoxication and viral infections, especially encephalitic alphavirus infections. The compound 4210 showed antiviral efficacy by up regulation type 1 interferon (IFN) specifically IFN-β. The compound 4210 was designed and synthesized by structure-based approach targeting host adaptor protein, myeloid differentiation primary response protein 88 (MyD88). Besides antiviral effect, the compound 4210 also demonstrated therapeutic efficacy for treating inflammatory syndrome associated with Gram positive bacterial infections such as exposure to staphylococcal enterotoxin B (SEB) induced toxic shock syndrome (TSS) in mice and can potentially be used in clinical set up for sepsis and septic shock. In addition, compound 4210 has therapeutic applications for treatment of sepsis and septic shock triggered by exposure to other biological threat agents such as *Francisella tularensis* or *Burkholderia mullei* known to cause tularemia and glanders respectively. Compound 4210 has potential for a broad spectrum therapeutic use.

With more than 20 viruses known to cause human encephalitis, alphaviruses, which are in the family of Togaviridae, contain three viruses: Venezuelan equine encephalitis virus (VEEV), Eastern equine encephalitis (EEEV) and Western equine encephalitis virus (WEEV). They are plus-strand RNA viruses that represent a significant public health threat as both emerging infectious diseases and possible agents for bioterrorism due to their morbidity and mortality in humans, high infectivity in aerosols, ease of production and considerate stability. As a result, these encephalitic alphaviruses are defined as Category B select agents by the Centers for Disease Control and Prevention. There are currently no FDA-licensed vaccines or therapeutics to protect against VEEV, EEEV and WEEV infections in humans. Neurovirulence of the alphaviruses associates with efficient and rapid spread of virus throughout the neurons of the central nervous system (CNS) resulting in pathogenesis and death of neural cells. Over the years myriad of studies in mice lacking interferon receptor I (IFNAR-I), IFN-β or Stat1 α or expressing tissue-specific type-I-IFN transgenes have demonstrated that type I IFNs control infections with a broad spectrum of viruses, including alphaviruses. It is also well established that cells exposed to type I IFNs display pronounced resistance to virus replication, as animal defective in IFN production are highly sensitive to infection. Antiviral function of type I family of interferons (IFN-α) isotypes and IFN-β, is due to both direct effects (i.e., mediating resistance viruses) and indirect effects (i.e., immune-stimulation), has led to the approval of IFN-α for clinical use (e.g., treatment of chronic hepatitis B or C). Thus, host directed induction of type 1 response is an extreme powerful antiviral response that is cable of controlling most, if not all, virus infections in the absence of adaptive immunity. However, viruses can still replicate and cause diseases in vivo, because they have some strategy for at least partially circumventing the IFN response. Therefore, up regulation of type 1 IFN response through host immune signaling component is a novel approach for antiviral therapy.

Production of type I IFNs requires the recognition of viral pathogen associated molecular patterns (PAMPs) by host toll-like receptors (TLRs) and retinoic acid inducible (RIG-I)-like receptors (RLRs) and/or melanoma differentiation-associated gene-5 (MDA-5) like receptors. In TLR signaling, intracellular adaptor protein MyD88 plays a critical role for the activation of all TLRs except TLR3 for inducing host pro-inflammatory response. Conversely, the absence of MyD88 enhances TLR3-dependent IFN-β (TLR3/Toll-interleukin receptor (RIR) domain containing adaptor-inducing IFN-I (RRIF) mediated signaling) suggesting that MyD88 negatively regulates anti-viral immune response. MyD88 can associate directly or indirectly with other signaling proteins that are involved in pro-inflammatory signaling.

Our results provide evidence that, by targeting MyD88, compound 4210 inhibited inflammatory cytokine production in human primary cells and increased therapeutic efficacy in mice with exposure to toxins of both gram-positive and gram-negative pathogens. Also in the context of viral infections such as alphavirus infections the compound 4210 treatment increased host-directed antiviral immunity by up regulation of IFN-β and RANTES production.

Materials and Methods

Compound 4210

The synthesis of compound 4210 was the same for both treatment of both viruses and bacterial pathogens.

Trans-cyclohexane-1,4-dicarboxylic acid (0.52 g, 3.0 mmol) was stirred in neat thionyl chloride (30 mL) at 90° C. for 6 h. The solvent was evaporated and the residue was placed under a nitrogen atmosphere. (S)-3-methyl-2-((3-phenylpropyl)amino)-1-(pyrrolidin-1-yl)butan-1-one (17) (1.7 g, 6.0 mmol) in dry tetrahydrofurane (30 mL) and diisopropylethylamine (2.1 mL, 1.6 g, 12 mmol) were added and the solution stirred at room temperature for 24 h. The reaction mixture was diluted with ethyl acetate (0.15 L), extracted with NaOH 1.0 M (50 mL), HCl 1.2 M (50 mL) and sat. $NaHCO_3$ (50 mL) and dried over $Na_2SO_4$. After evaporation of the solvents, the residue was purified by silica gel flash chromatography (acetone/$CH_2Cl_2$: 3→6%) affording compound 4210 (1.44 g, 67.0%) as a white foam. $^1H$ NMR (600 MHz, $CDCl_3$) δ 7.35-7.25 (t, J=7.4 Hz, 4H), 7.22-7.09 (m, 6H), 5.14-4.95 (d, J=10.7 Hz, 2H), 3.56-3.46 (m, 4H), 3.42-3.31 (m, 4H), 3.30-3.17 (m, 2H), 2.68-2.58 (m, 2H), 2.52-2.42 (m, 2H), 2.38-2.27 (m, 2H), 2.27-2.17 (m, 2H), 1.95-1.87 (m, 2H), 1.86-1.77 (m, 6H), 1.76-1.64 (m, 4H), 1.63-1.52 (m, 6H), 1.32-1.22 (m, 2H), 0.98-0.87 (d, J=6.5 Hz, 6H), 0.80-0.68 (d, J=6.8 Hz, 6H); $^{13}C$ NMR (150 MHz, $CDCl_3$) δ 176.37, 168.93, 140.70, 128.70, 128.33, 126.31, 77.16, 59.22, 46.70, 46.11, 42.84, 40.34, 33.18, 32.42, 29.12, 28.19, 27.40, 26.00, 24.10, 19.82, 18.02; Rf (acetone/$CH_2Cl_2$, 9%) 0.59; HRMS (ESI+) Calcd. for $[C_{44}H_{64}N_4O_4+H^+]$ 713.5000, found 713.5016.

Figure 1B:
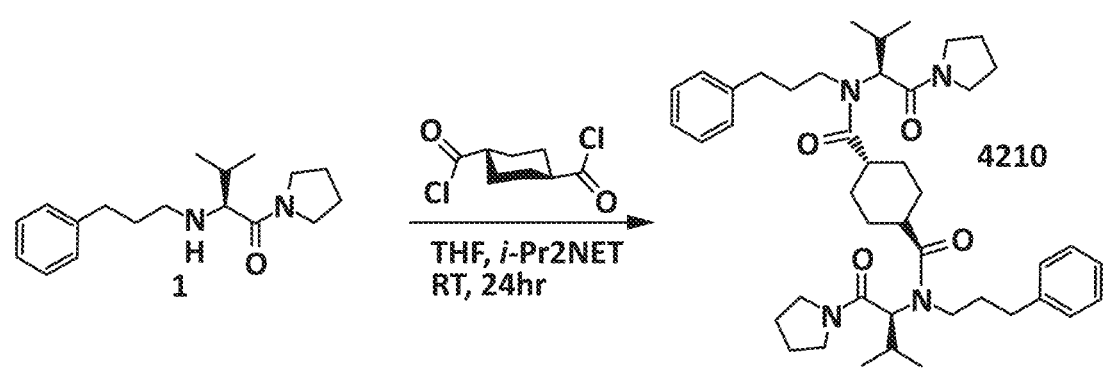
FIG. 1B shows the synthesis of molecule 4210.
Figure 1C:
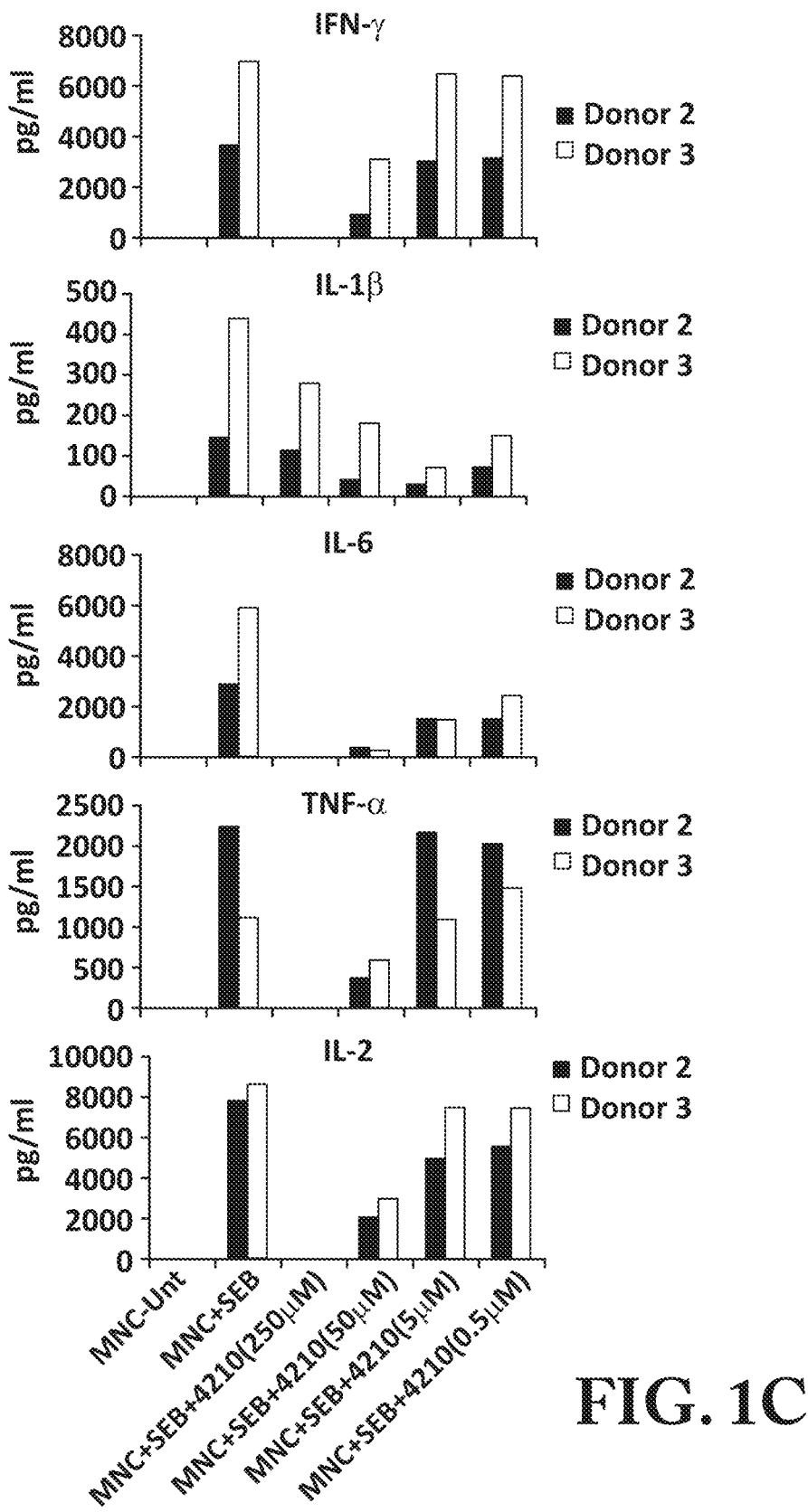
FIG. 1C is a graph series showing dose dependent inhibition of pro-inflammatory cytokine production by compound 4210 in primary PBMCs culture stimulated with SEB.

Compound 4210 was synthesized from Compound 1 (Hydrocinnamoyl-L-valyl-pyrrolidine) by covalent linkage via nonpolar cyclohexane See FIG. 1B.

Elements of the Supporting Information for 4210 Synthesis $^1H$ NMR spectra were recorded at 600 Mhz and $^{13}C$ NMR spectra at 150 MHz a Bruker Avance DRX-600 spectrometer equipped with a 5 mm QNP probe at 300 K. Chemical shifts of $^1H$ NMR and $^{13}C$ NMR are given in ppm (δ) with respect to trimethylsilane (TMS, δ=0.00) by using residual $CHCl_3$ proton or carbon signal as references (7.26 ppm, $^1H$ spectra, and 77.16 ppm for $^{13}C$ spectra). Coupling constants (J) are reported in hertz (Hz). Standard abbreviations indicating multiplicity were used as follows: s (singlet), d (doublet), t (triplet), m (multiplet). HRMS-ESI-TOF spectra were recorded by the mass spectroscopy service of the Scripps Research Institute using an Agilent ESI-TOF spectrometer.

Embodiment I

In the first embodiment molecule 4210 was shown to be beneficial in the treatment of bacterial infections, especially in treating staphylococcal enterotoxin B intoxication. The following is a description of the materials and methods associated with Embodiment I:

Reagents:

Staphylococcal enterotoxin B (SEB) and SEA was purchased from Porton Down,

Inc. (Salisbury, UK) and stored at −70° C. SEB was endotoxin free and prepared under GMP conditions. *Escherichia coli* LPS (055:B5) was purchased from Sigma-Aldrich (Saint Louis, Mo.). Pooled human AB sera were obtained from Pel-Freez (Brown Deer, Wis.). LPS extracts purified from *F. tularensis* and *B. mallei* used in this study were obtained from Dr. Dave Waag (USAMRIID) as described elsewhere. A cytometric bead array (CBA) kit was purchased from Pharmingen (San Diego, Calif.). The Meso Scale Discovery (MSD) multi spot array ultra-sensitive cytokine assay kit was purchased from MSD (Gaithersburg, Md.). Ficoll-Hypaque was purchased from GE Healthcare Biosciences (Piscataway, N.J.). Primary anti-MyD88 antibody was obtained from AnaSpec, Inc., (San Jose, Calif.) and Alexis Biochemicals (San Diego, Calif.). Anti-β-actin antibody was purchased from Cell Signaling Technology (Danvers, Mass.). Plasmid 12287 (pCMV-HA-MyD88) and plasmid 13093 (MyD88-flag) were purchased through an MTA agreement with Addgene (Cambridge, Mass.). HEK 293-SEAP-TLR4 cell was obtained from Invivogen (San Diego, Calif.). The transfection reagent lipofectamine 2000 was purchased from Invitrogen (Carlsbad, Calif.). All chemical reagents were purchased from Aldrich and used without further purification. The solvents were purchased from Fisher or J.T. Baker. All deuterated solvents were purchased from Cambridge Isotope Laboratories, Inc.

Mice used for Staphylococcal Testing

Pathogen-free, 12-16 weeks old BALB/c and C57BL/6 mice were obtained from Charles River (NCI-Frederick, Frederick, Md.). $MyD88^{-/-}$ were obtained from Charles River Laboratory as described elsewhere.

Cell Isolation and Purification for Staphylococcal Testing

Peripheral blood mononuclear cells (PBMCs) were obtained from consenting healthy donors in accordance with an Institutional Review Board-approved research donor protocol. PBMCs were isolated by standard density gradient centrifugation with Ficoll-Hypaque, harvested from the interface, washed, and re-suspended in RPMI 1640 medium. Isolated cell populations were >98% purity.

Cytokine Analysis for Testing Staphylococcal Enterotoxin Exposure

Cell cultures were incubated (37° C., 5% $CO_2$) for 16 h. Cytokines in culture supernatants were measured by a CBA kit using captured beads coated with antibodies specific for cytokines and flow cytometry analysis as described elsewhere. Cytokine measurements were confirmed by dilution of culture supernatant using Human Inflammation and Th1/Th2 CBA kits and acquiring 1800 beads. We also used Meso Scale Discovery (MSD) multi spot array ultrasensitive cytokine assay kit for measuring cytokines in culture supernatants (according to the manufacturer's protocol).

Western Blot Analysis for Testing Role of MyD88 with Exposure to Staphylococcal Enterotoxin B The transfected cells were chilled on ice for 5 min before being pelleted into fresh 1.5 ml centrifuge tubes. Membrane and cytoplasm separation was done by suspending the pellets in 50 μl of lysis buffer (Active Motif) in the presence of DTT, protease inhibitors and phosphatase inhibitors and incubated on ice for 30-60 min. The membrane fraction was collected by centrifuging the lysates at 14000×g for 20 min. The supernatant contained the cytoplasmic fraction. Samples containing 10 μg of total cytoplasmic proteins were separated by gel electrophoresis and transferred to nitrocellulose membranes. The membranes were blocked overnight in 1×Tris-buffered saline (TBS) containing 0.1% Tween-20 (TBST) and 3% bovine serum albumin at 4° C. The membranes were washed extensively with 1×TBST buffer and then probed with anti-MyD88 polyclonal antibody followed by horseradish peroxidase-conjugated secondary antibody (goat anti-rabbit). After additional rinsing with 1×TBST buffer, the membranes were exposed to a chemiluminescent substrate in the presence of hydrogen peroxide, using Immun-Star WesternC Chemiluminescence kit (Bio-Rad). A VersaDoc Model 4000 (BioRad) imaging system was used to capture the image.

Cell Culture and Transfections for Analyzing MyD88 Signaling and the Role of MyD88 Inhibitor 4210 in Signaling Inhibition Human embryonic kidney (HEK) 293-SEAP-TLR4 cells were cultured in EMEM, supplemented with 10% fetal bovine serum (FBS) (Invitrogen, Carlsbad, Calif.), and grown in a 37° C. humidified atmosphere of 5% $CO_2$. For co-immunoprecipitation of MyD88-Flag/HA-MyD88, HEK293-SEAP-TLR4 cells were cultured in 6-well plates and transfected by lipofectamine 2000 (Invitrogen) method with 4 µg of the appropriate plasmids according to the manufacturer's instructions. The compound 4210 was added to the medium 6 h after transfection. Six h after transfection, cells were cultured with LPS in the presence or absence of compound 4210.

Co-Immunoprecipitation Assay for Analyzing the Role of MyD88 Dimerization with SEB Exposure in Staphylococcal Enterotoxin B Exposure Testing HEK293-SEAP-TLR4 cells (transfected or Mock) were collected 48 h after transfection, washed with 2 ml of ice-cold PBS, and lysed in 80 µl of buffer (50mM HEPES, pH7.4). Cells were pelleted by centrifugation at 10,000×g for 10 min at 4° C., and cytosolic fractions were collected for immunoprecipitation. Cell extracts (1 mg total proteins) were incubated with 2 μg of mouse anti-Flag M2 conjugated with agarose attached to magnetic beads (Sigma-Aldrich) for 16 h under constant shaking at 4° C. Agarose bead-bound immunocomplexes were separated by a magnetic separator, washed three times, and eluted in SDS-PAGE sample buffer for western blot analysis.

Secreted Alkaline Phosphatase (SEAP) Assay for Determining the Specificity of Compound 4210 to MyD88 Signaling of Staphylococcal Enterotoxin Exposure Testing TLR4/MD-2/NF-kB/SEAPorter HEK 293 cells ($5\times10^5$ cells/ml/well) were cultured with LPS (1 μg/ml), with varying concentrations of compound 4210 in a 96-well plate and incubated at 37° C. for 16 h. The culture supernatant was collected and centrifuged to remove any cell debris. The Great EscAPe SEAP assay from Clonetech was used to determine the amount of alkaline phosphatase secreted into the supernatant. A 1× dilution buffer was prepared from a 5× stock solution and 75 μl of the 1× dilution buffer was mixed with 25 μl of the supernatant, incubated for 30 min at 65° C. to inactivate endogenous alkaline phosphatase. The samples were placed on ice for 3 min and then equilibrated at room temperature. SEAP substrate solution (100 μl) was added to each sample and read at 10 min intervals using a chemiluminescence reader.

Results for Staphylococcal Enterotoxin Exposure Testing

Design and Synthesis of Compound 4210

We aimed to increase the potency of the earlier reported compound 1 (shown in FIG. 1B) by covalently linking as a dimer for greater flexibility to interact with target domain of MyD88. For this, we covalently linked compound 1 by a non-polar cyclohexane ring aiming that a six-member heterocycle ring would increase flexibility for binding to the exposed BB-loop of the TIR domain of MyD88. We did this to recruit MyD88 as a dimer for signal transduction. The compound 4210 was synthesized from the compound 1 as shown in materials and methods (See FIG. 1B). When assessed in biological assays and in vivo dimeric compound 4210 with a non-polar linker in the spacer region between the monomer significantly increased the potency of the molecule as an inhibitor of MyD88-signaling as described below. (For further discussion of compound 1, see Kissner T. L., Moisan L., Mann E., Alam S., Ruthel G., et al. (2011) A small molecule that mimics the BB-loop in the Toll/IL-1 receptor domain of MyD88 attenuates staphylococcal enterotoxin B induced pro-inflammatory cytokine production and toxicity in mice. (J. Biol. Chem. 286:31385 -31396, incorporated herein by reference.)

Inhibition of Pro-Inflammatory Cytokine Production of Human PBMCs with Exposure to SEB, LPS or Killed *B. mallei* in the Presence of Compound 4210

To assess the biological effect of compound 4210 on the inhibition of pro-inflammatory cytokine production of primary human cells, peripheral blood mononuclear cells (PBMCs) were cultured with SEB, or LPS from *F. tularensis* or *E. coli,* or with whole *B. mallei* (irradiated) in the presence of compound 4210. The cultures were incubated for 16 h and culture supernatants were collected for measuring cytokines. The release of pro-inflammatory cytokines such as IL-1β, IL-6, IL-2, TNF-α and INF-γ in culture supernatant was inhibited in a dose dependent manner in the presence of the compound 4210 (FIG. 1C). The average inhibitory concentration ($IC_{50}$) of compound 4210 appeared to be 1 μM to 50 μM for most of the pro-inflammatory cytokines tested with some variation in response from donor to donor (FIG. 2A). The compound 4210 was upgraded from compound 1.

To prove that the anti-inflammatory effect of compound 4210 was superior that of compound 1, we tested for cytokine inhibitory effect by direct comparison of compound 1 and compound 4210 under the same conditions from PBMCs of two additional normal donors stimulated with SEB. In donor 1, the $IC_{50}$ of compound 4210 for IFN-γ, IL-1β, IL-6, and TNF-α were 0.30 μM, 0.37 μM , 0.4 μM and 0.37 μM respectively, whereas ($IC_{50}$) of compound 1 for IFN-γ, IL-1β, IL-6, and TNF-α were 41 μM, 35 μM , 14 μM and 19 μM respectively (FIG. 2C). Similar results were observed with donor 2 (FIG. 2C). These results demonstrate that the compound 4210 is indeed an enhanced version of compound 1. Besides SEB, the compound 4210 also inhibited cytokine production when primary PBMCs cultured with LPS (*F. tularensis* or *E. coli*), or killed *B. mallei* (FIG. 2B and 2D) These results suggest that compound 4210 was capable of inhibiting SEB, *B. mallei,* or LPS (*F. tularensis* or *E. coli*)-induced pro-inflammatory cytokine production. These ex vivo cytokine inhibition data are consistent with our earlier findings which demonstrated MyD88-mediated pro-inflammatory cytokine response upon SEB or SEA exposure in mice, and cytokine production were inhibited in $MyD88^{-/-}$ mice.

Inhibition of MyD88-Specific Signaling by Compound 4210

To confirm the inhibitory effect of compound 4210 on MyD88 signaling, we utilized a cell-based reporter assay. A stable co-transfected (TLR4-MD2-NF-kB/SEAPorter™) HEK 293 cell line was used to detect a MyD88-mediated NF-kB driven SEAP reporter response induced by LPS (TLR4-ligand). The inhibitory concentration ($IC_{50}$) of compound 4210 as shown in FIG. 3A was determined from the dose dependent inhibition curve (FIG. 3B). Compound 4210 inhibited the LPS (*E. coli, F. tularensis* or *B. mallei*) -induced MyD88-mediated (via TLR4-MD2-MyD88-NF-kB-SEAP) SEAP response in a dose-dependent manner (FIG. 3B). It is important to note that $IC_{50}$ of SEAP reporter activity and cytokine inhibition was comparable (FIG. 2B and FIG. 3A). Further, to prove that the enhanced effect and mechanism of compound 4210 upgraded from compound 1, we tested a direct comparison of compound 1 and compound 4210 under the same conditions in SEAP reporter assay. The compound 4210 demonstrated a dose dependent inhibition of SEAP reporter expression at much lower concentration than compound 1 (FIG. 5D). The calculated $IC_{50}$ value of SEAP response of compound 4210 activated with LPS (*E.

Figure 5A:
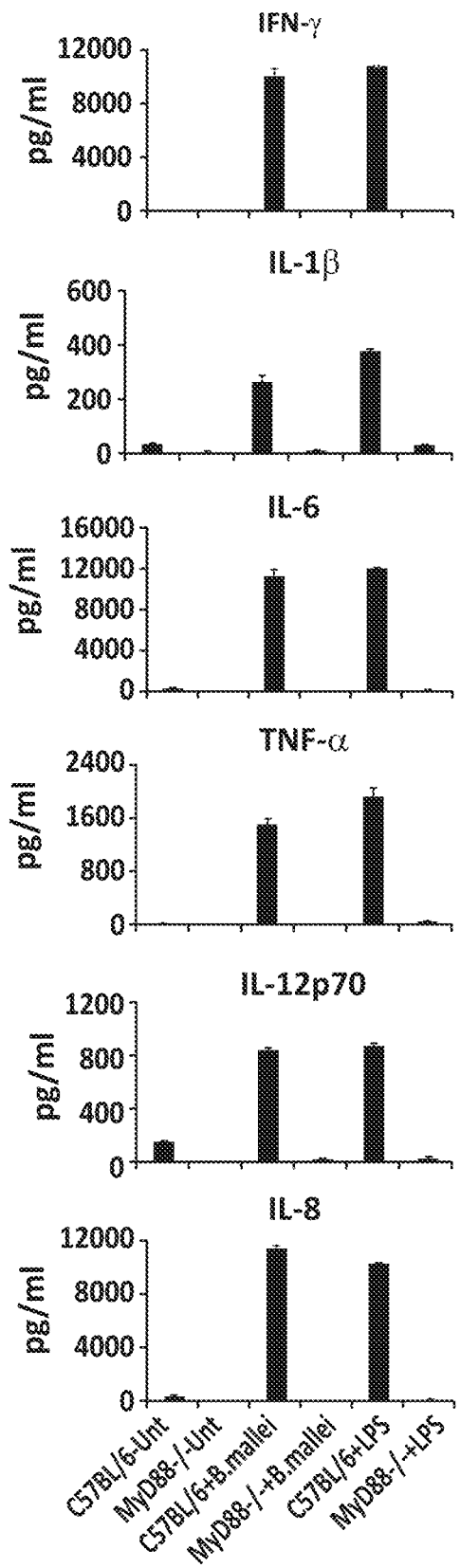
FIG. 5A is a graph series showing cytokine response (pg/ml) in mouse spleen cells with exposure to *B. mallei* or LPS in C57BL/6 (wild type) and MyD88$^{-/-}$ mice.
Figure 5B:
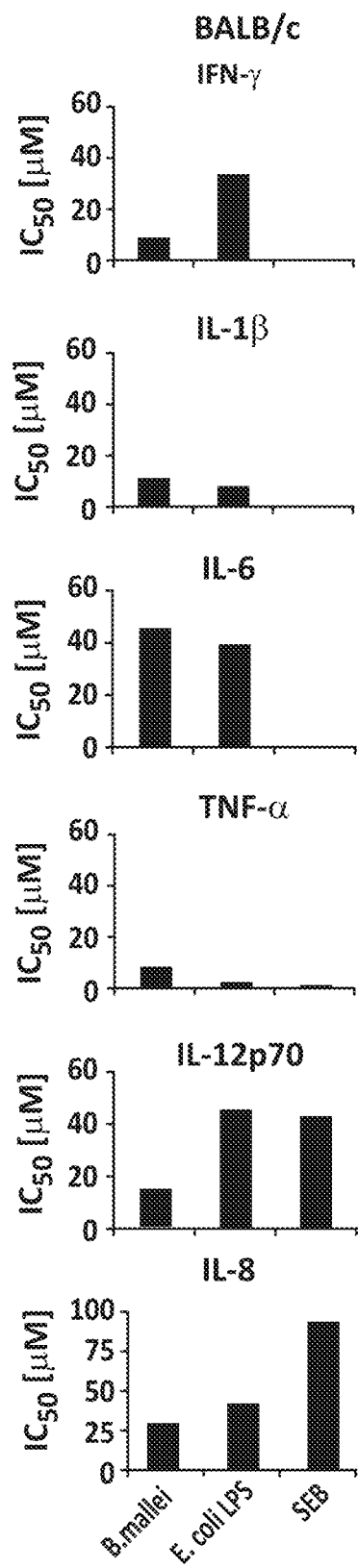
FIG. 5B is a graph series showing cytokine inhibition in mouse spleen cell culture of BALB/c mice as $IC_{50}$ concentration.
Figure 5C:
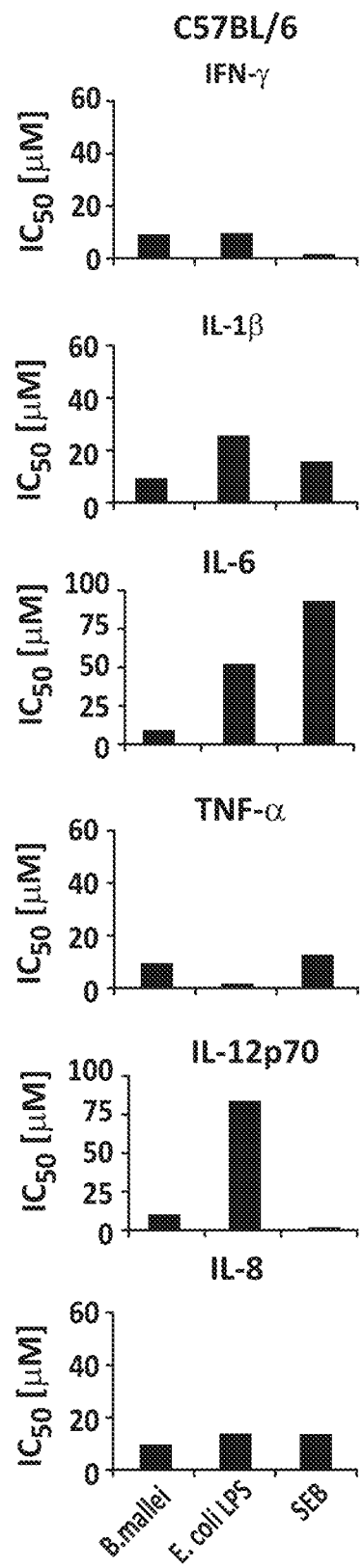
FIG. 5C is a graph series showing cytokine response in C57BL/6 mice in the presence of compound 4210 as $IC_{50}$ concentration.
Figure 5D:
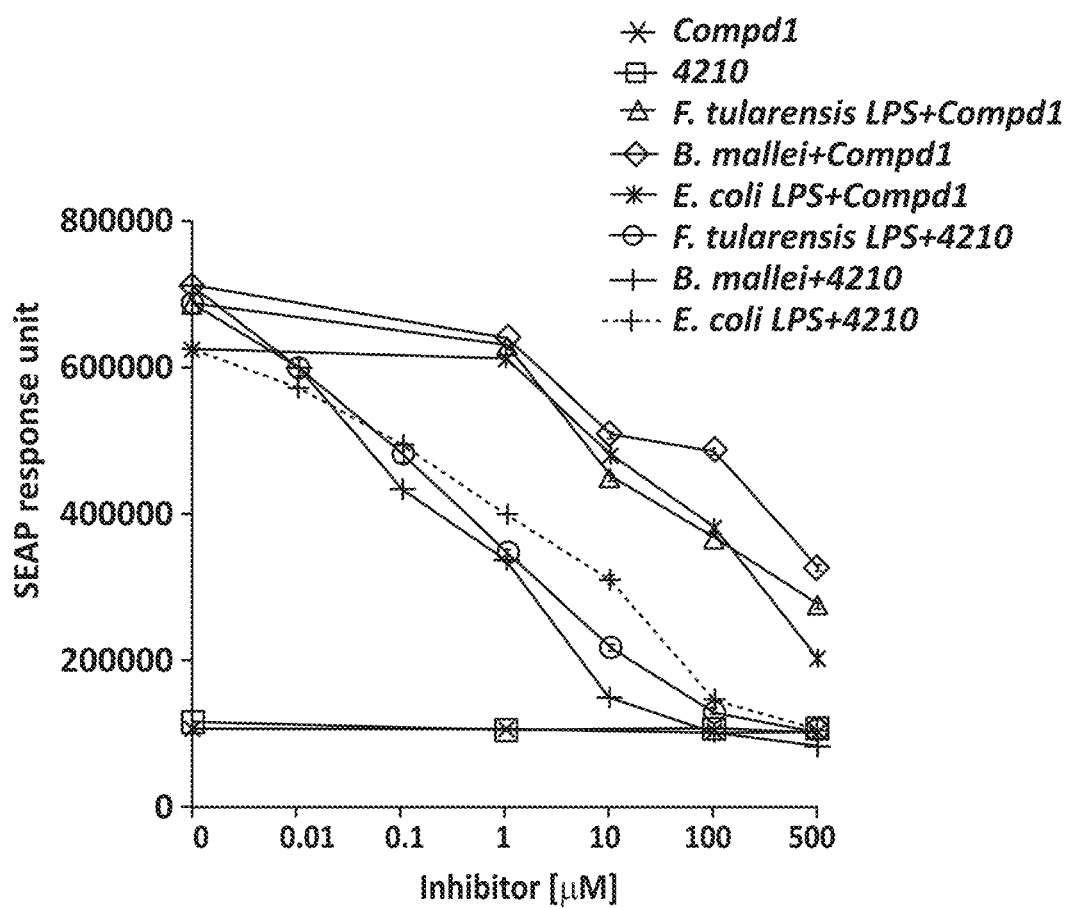
FIG. 5D is a graph showing inhibition of SEAP reporter activity by compound 1 and compound 4210 stimulated with LPS (*F. tularensis* or *E. coli*) or *B. mallei*.
Figure 6A:
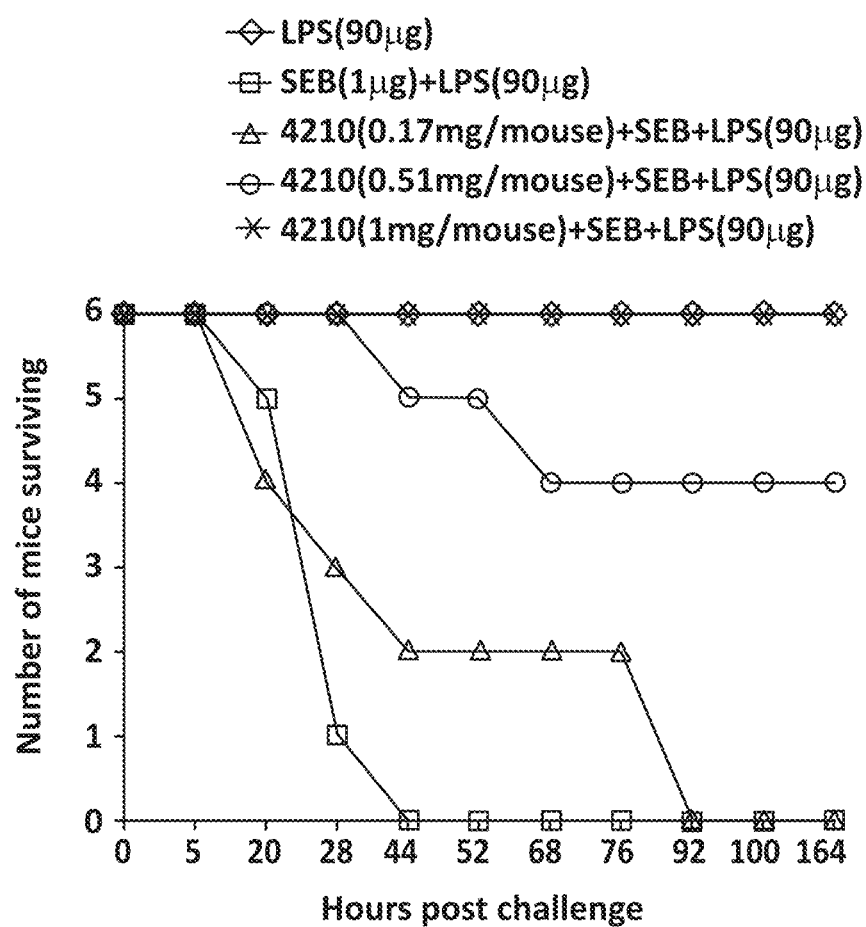
FIG. 6A is a graph showing survivability of mice with pre-treatment of compound 4210.
Figure 6B:
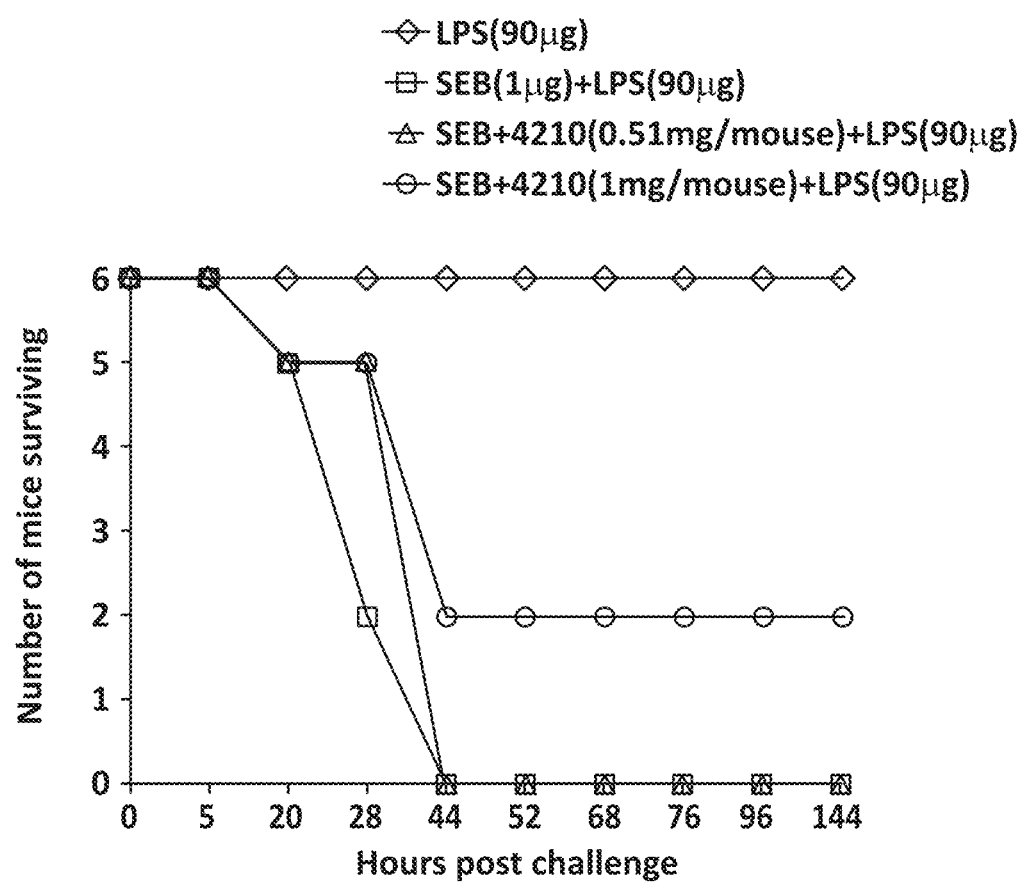
FIG. 6B is a graph showing survivability of mice with post-exposure to SEB; p
Figure 6C:
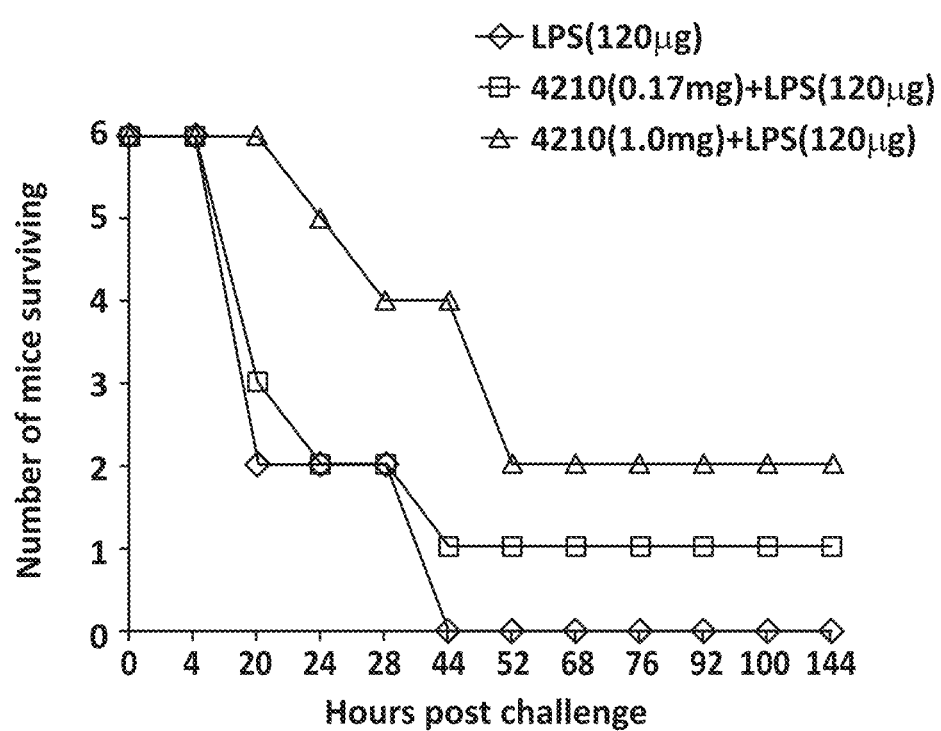
FIG. 6C is a graph showing survivability of mice with pre-treatment of compound 4210 to lethal LPS (120 µg) exposure.
Figure 6D:
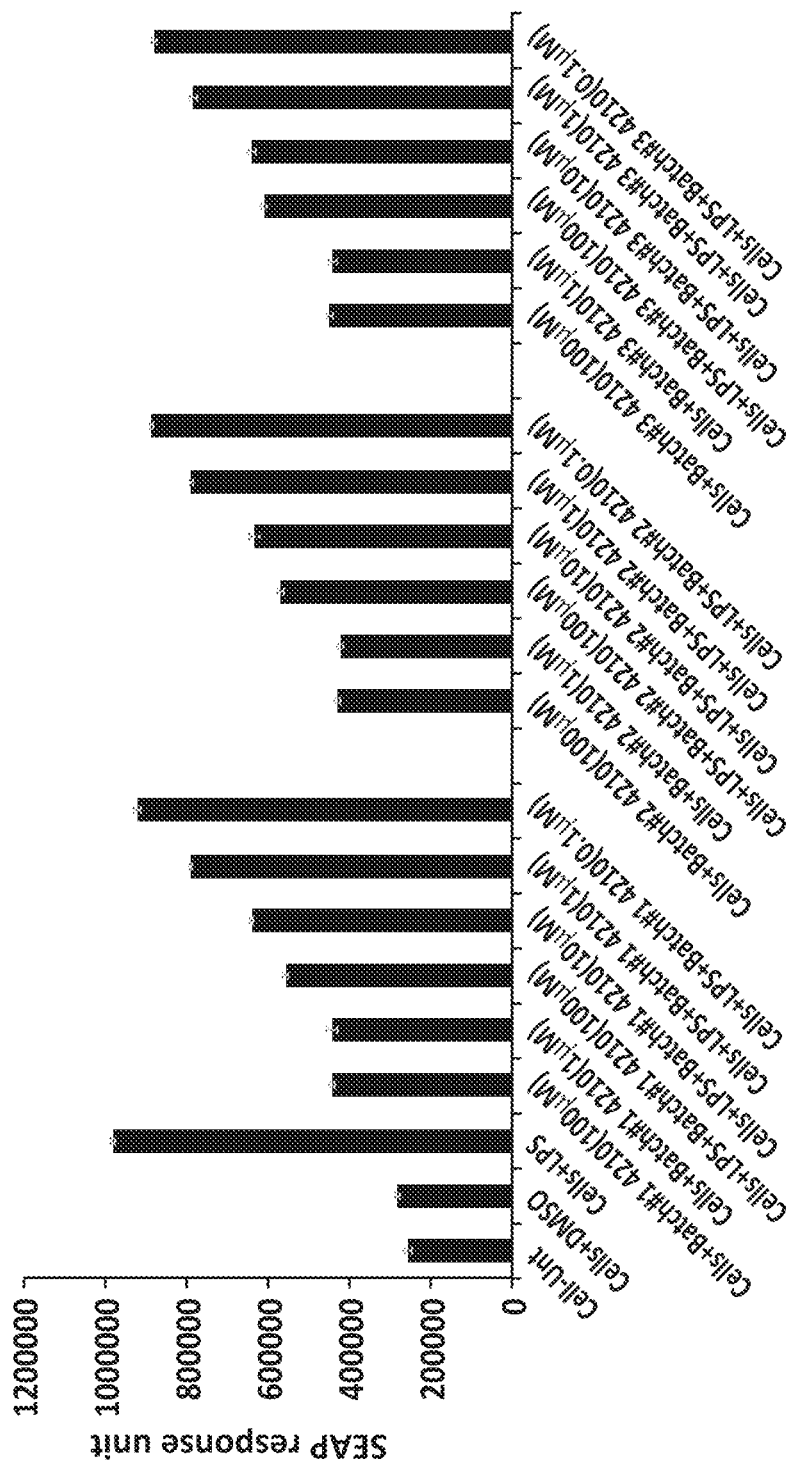
FIG. 6D is a graph showing consistent biological results (QA/QC) of different batches of compound 4210 synthesized at different times.

*coli, F. tularensis*) and *B. mallei* were 1 µM, 0.47 µM and 6 µM respectively compared to $IC_{50}$ Compound 1 stimulated with LPS (*E. coli, F. tularensis*) and *B. mallei* were 87 µM, 270 µM and 180 µM respectively (FIG. 5D). We also tested the various batches of compound 4210 synthesized at different times for quality assurance and quality control (QA/QC) by SEAP reporter assay. The compound 4210 showed a consistent dose dependent inhibition of MyD88-specific signaling (SEAP) reporter expression (FIG. 6D). These results suggest that compound 4210 by targeting specifically MyD88 inhibited downstream NF-kB driven SEAP reporter activity.

Inhibition of Newly Expressed MyD88-MyD88 Association in the Presence of Compound 4210

Figure 2A:
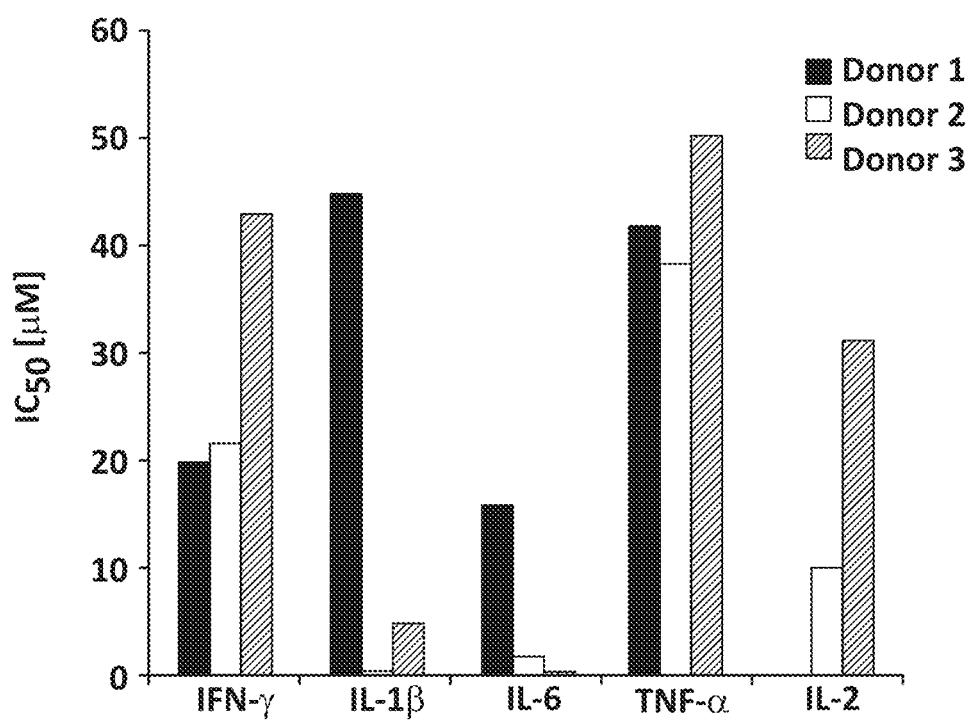
FIG. 2A is a graph of the inhibition of pro-inflammatory cytokines with exposure to SEB, data being presented as $IC_{50}$.
Figure 2B:
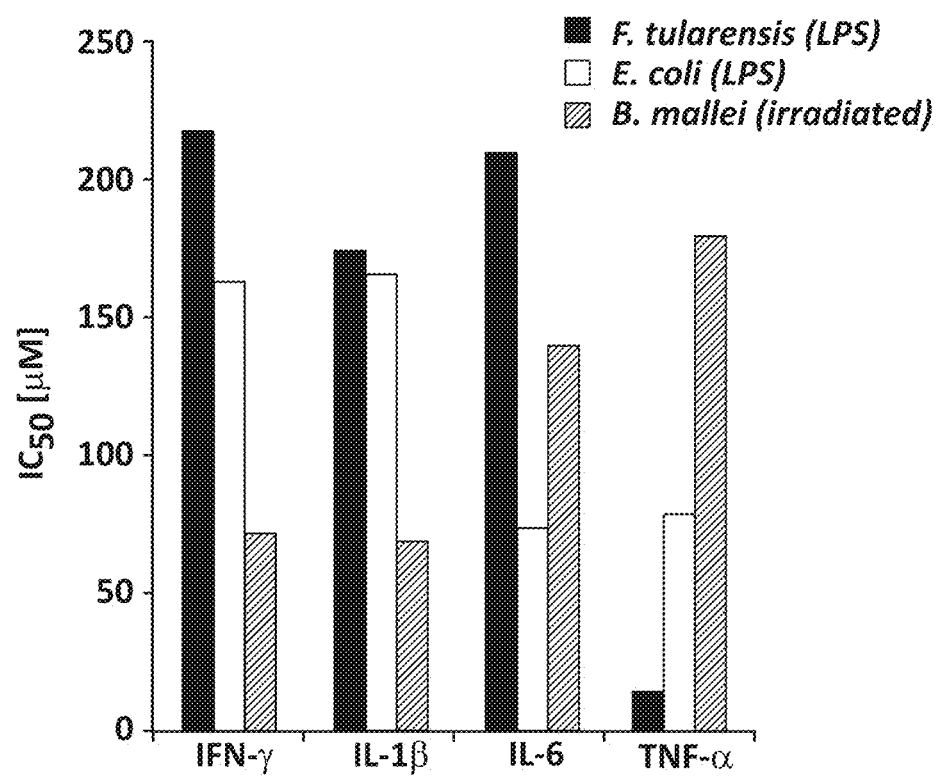
FIG. 2B is a graph of the inhibition of pro-inflammatory cytokines with exposure to LPS extracted from *F. tularensis* or *E. coli* or Irradiated *B. mallei*, data being presented as $IC_{50}$.
Figure 2C:
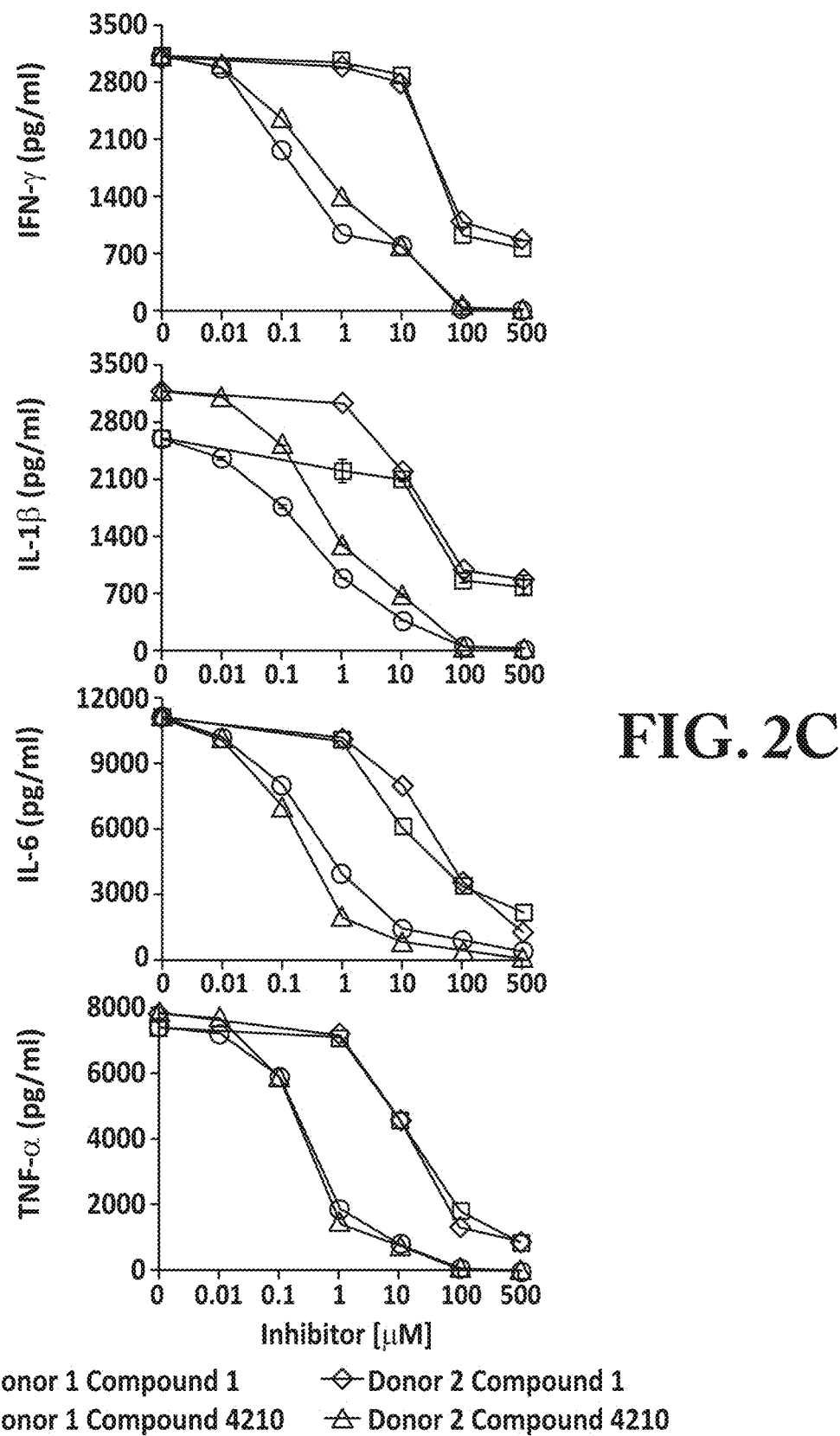
FIG. 2C is a series of graphs showing pro-inflammatory cytokine inhibition by compound 1 and compound 4210 in primary culture of PBMCs stimulated with SEB.
Figure 2D:
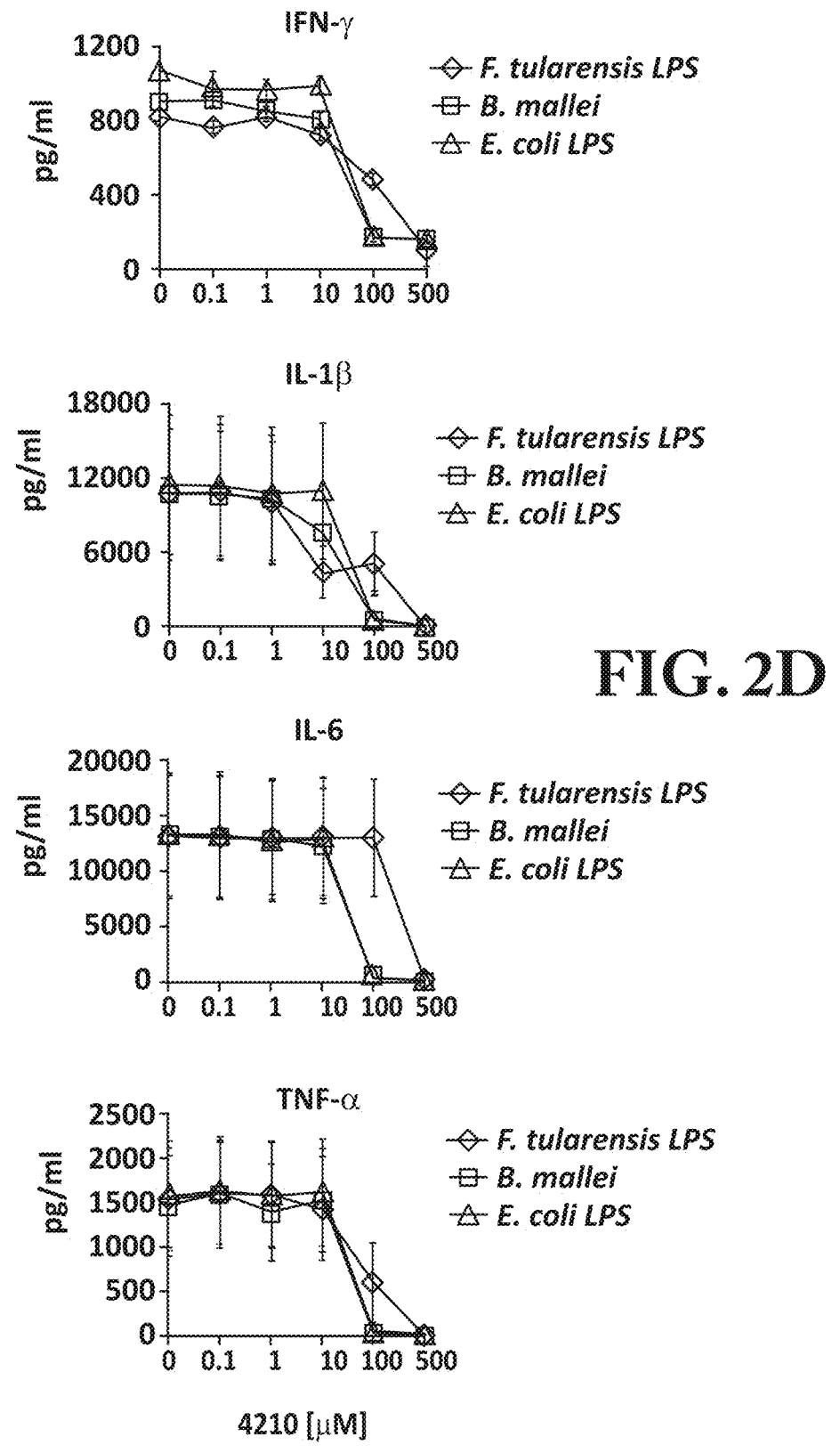

We previously demonstrated that SEB stimulation up regulates MyD88 in primary human cells. Next we tested if compound 4210 targets newly synthesized MyD88 when activated with ligand such as LPS. To follow this, MyD88 knockout cell line HEK 293-I13A cells were co-transfected with plasmids pCMV-HA-MyD88 and MyD88-Flag and 6 h later cells were treated with varying concentrations of compound 4210. In a co-immunoprecipitation assay using anti-Flag antibody, followed by SDS-PAGE and immunoblot analysis with anti-MyD88 antibody, an increase in accumulation of the newly expressed MyD88 (31 kDa) protein was observed in a dose-dependent manner (FIG. 4A) compared to untreated cells. Results shown in FIG. 4A, suggest that in the presence of compound 4210, newly expressed MyD88 dimer formation was inhibited and maximum inhibition was observed in between 10 µM to 100 µM. The 31 kDa MyD88 band was further confirmed by re-probing with anti-HA antibody, and the results showed a compound 4210 dose dependent results (FIG. 4B). These data demonstrate that Flag-MyD88 and HA-MyD88 association was inhibited by the compound 4210. Interestingly these data are consistent with cytokine inhibition and SEAP reporter expression (FIG. 2 and FIG. 3). In agreement with earlier reports, these results indicate that ligand binding to TLR4 induced higher level of MyD88 expression, which allowed it to associate through its TIR domain for homodimer formation whereas in the presence of compound 4210 by targeting TIR domain, it inhibited dimerization of MyD88. It is likely the possible mode of binding of the dimeric compound 4210 to MyD88 as 1:2 molar ratio (4210:MyD88), since MyD88 is recruited as dimer for signal transduction and thereby increased inhibition efficiency for the downstream signal transduction for pro-inflammatory cytokine responses.

Cytokine Inhibition by Compound 4210 with Exposure to SEB, LPS or *B. mallei* in Mouse Spleen Cell Cultures Our earlier results showed that compound 4210 strongly inhibited cytokine inhibition in human primary cells with exposure to SEB, LPS, or *B. mallei*, (FIG. 2), and targeted to newly synthesized MyD88 induced by LPS (FIG. 3 and FIG. 4). As MyD88 is involved in pro-inflammatory cytokine production with exposure to gram-negative pathogens or LPS, we next examined the effect of compound 4210 on cytokine inhibition in spleen cells of wild-type C57BL/6 and MyD88$^{-/-}$ mice (C57BL/6 background) with exposure to LPS and *B. mallei*. As expected, cytokine production was abrogated in spleen cell cultures isolated from MyD88$^{-/-}$ mice (FIG. 5A), while wild type C57BL/6 produced pro-inflammatory cytokines. These results were consistent with our earlier report in which we described abrogation of pro-inflammatory cytokine production in MyD88$^{-/-}$ mice with exposure to SEB. Next, we examined whether treatment of compound 4210 would inhibit cytokine production in spleen cells of wild type BALB/c as well as C57BL/6 mice. Results shown in FIG. 5B and FIG. 5C demonstrated that compound 4210 inhibited most of the pro-inflammatory cytokine production with exposure to SEB, *E. coli* LPS, or *B. mallei* in spleen cell cultures. It is important to note that $IC_{50}$ values varied with different cytokines, which is not unusual, because cytokine response varies with specificity of the cell types and kinetics. These results suggest that compound 4210 by specifically targeting MyD88 inhibited the cytokine production in spleen cell cultures of both BALB/C and C57BL/6 mice exposed to both gram-positive and gram-negative pathogens or pathogen derived components such as *B. mallei*, LPS or SEB. Thus, similar to human primary PBMC culture, compound 4210 by targeting specifically MyD88 inhibited cytokine signaling in spleen cells of mice.

In Vivo Efficacy of Compound 4210: Attenuation of SEB or LPS-Induced Toxicity in Mice Next, we examined whether the targeting of compound 4210 with TIR domain of MyD88 inhibited cytokine production as we observed in ex vivo culture in mouse spleen cells and if it could protect animals from toxic shock induced death with exposure to SEB or LPS. To address this, we used the LPS potentiation (sub lethal dose) model of SEB toxicity in mice. BALB/c mice (n=6) were injected with different amounts of compound 4210 (0.17 mg, 0.51 mg or 1 mg) and 30 min later they were treated with SEB (1 µg) equivalent to (2 $LD_{50}$), followed by LPS another 2 h later. All animals in the study, not treated, died by 44 h (FIGS. 6A and 6B). In contrast, mice treated with compound 4210 showed dose-dependent protection. Mice that were treated with compound 4210 at concentrations of 0.17 mg had (33%) and 0.51 mg had (66%) survivability, whereas mice that were treated with compound 4210 at 1 mg were completely protected (p=0.05) (FIG. 6A). Post-exposure treatment (first SEB exposure followed by compound 4210 treatment with 0.17 mg or 0.51 mg and 2 h later LPS) delayed in death and 33% protection was observed at 1 mg (FIG. 6B). These results indicate that compound 4210 has in vivo therapeutic efficacy against SEB intoxication. We also examined in vivo efficacy of compound 4210 against toxicity to lethal dose (120 µg) with only endotoxin (LPS) exposure. Our results showed that in comparison to lethal LPS-treated mice, administration of a single dose of compound 4210 (1 mg) delayed death and 33% of mice were protected from lethal endotoxic shock (FIG. 6C).

Discussion of Embodiment 1

Gram-positive and gram-negative pathogens or pathogen-derived component activates pro-inflammatory response via MyD88-mediated signaling. Our previous studies demonstrated that MyD88-mediated pro-inflammatory cytokine signaling is critical to SEB toxicity. Here, we have shown that a synthetic molecule designed that resembles BB-loop like structure of MyD88 with dual functional groups (dimer) connected with a non-polar cyclohexane linker significantly enhanced in vivo efficacy (50 mg/kg) in attenuating SEB as well as LPS toxicity compared to compound 1. Compound 4210 exhibits anti-inflammatory properties that is effective in limiting pro-inflammatory cytokine signaling when exposed to both enterotoxin and endotoxin. Thus, compound 4210 has a broad-spectrum therapeutic use.

TIR domain constitutive association of dimer formation is essential for MyD88-mediated signaling with ligand binding to TLRs. Earlier results have shown that MHC class II plays a fundamental role in driving TLR-mediated inflammatory responses and MHC class II negative cells do not up regulate MyD88 when stimulated with MHC class II ligands. It has been reported that deficiency in MHC class II impaired TLR-triggered production of inflammatory cytokines in macrophages and DCs, and this protected mice from lethal challenge with TLR ligands and live gram-negative bacteria. Furthermore, it has been shown that in lysates of HEK293 cells over expressing HLA-DR, radio-labeled recombinant TLR-2 protein precipitates in vitro together with HLA-DR protein immune-precipitated with anti HLA-DR. So, TLR-2 was proposed to be associated with HLA-DR. However, whether or not TLR-2 and HLA-DR interact physically has yet to be determined. Clinical results have shown that HLA-DR expression in peripheral blood monocytes is much lower in patients with septic shock than in normal subjects. Such patients release much less TNF-α and IL-1β than do normal subjects in response to LPS. These results suggest the involvement of TLR and MHC-mediated responses MyD88 for pro-inflammatory signaling which likely is an outcome in septic shock.

Our earlier results demonstrated that small molecules mimicking BB-loop structure of MyD88 interfere with pro-inflammatory signaling with exposure to SEB, LPS or SEB+LPS in ex vivo primary cells and in mice. We also reported that a dimeric compound EM-163 with two compound 1 covalently linked with an aromatic ring (pyridine) linker had increased efficacy ex vivo in mice over the compound 1. EM-163 had a non-polar and flat (rigid) structural characteristic because of aromatic ring and less flexibility, which likely requires a high concentration for a specific mode of binding in solution. In this study, our results showed that compound 4210 had an increase in efficacy both ex vivo ($IC_{50}$ 1-50 µM compared to compound EM-163 $IC_{50}$ 50-400 µM). Concurrent with ex vivo cytokine inhibition data, administration of compound 4210 in mice increased therapeutic efficacy (1 mg) compared to compound EM-163 (1.7 mg) from toxic shock-induced death with lethal SEB challenge. It may be that compound 4210, with a non-polar cyclohexane linker between the covalently linked compound 1, provided more flexibility and facilitated binding to exposed BB-loop residues of MyD88. It, thereby, prevented association of MyD88-MyD88 dimer formation. It may be possible that the binding of dimeric compound 4210 to MyD88 at 1:2 molar ratio (4210:MyD88) increased inhibition efficiency and therapeutic efficacy.

Besides SEB, compound 4210 appeared to be effective in inhibiting pro-inflammatory response to endotoxin exposure of gram-negative pathogens, such as *F. tularensis* or *E. coli* or *B. mallei* in primary cultures of mice and humans. The combinations of endotoxins and enterotoxins exposure have been shown to have severe consequences. Critically ill patients may be exposed to endotoxin from gram-negative organisms and enterotoxin from toxin-producing gram-positive organisms, even if the organisms are simply colonizing the patients. The dual exposure is intimately involved in the genesis of endotoxin-enterotoxin double hit, which would lead to profound clinical consequences. Our results showed that compound 4210 was found to be equally effective in limiting pro-inflammatory response to both endotoxin as well as enterotoxin exposure. In a clinical scenario compound 4210 is effective in restricting amplification of the MyD88-mediated pro-inflammatory signaling cascade. Compound 4210 has been shown to have broad-spectrum use.

EXAMPLES

Embodiment 1

Please refer to the figure descriptions 2-6 below for examples of the Embodiment 1 of the present invention.

FIG. 1C. Dose Dependent Inhibition of Pro-Inflammatory Cytokine Production by Compound 4210 in Primary PBMCs Culture Stimulated with SEB PBMCs ($1\times10^6$) from two normal donors (donor 2 and donor 3 as shown in FIG. 2A) were cultured for 20 h with SEB (200 ng) with or without compound 4210 (250 to 0.5 μM) treatment. The culture supernatants were collected and measured for cytokine by CBA assay as described in materials and methods. The data presented as dose dependent inhibition of cytokine production (pg/ml) and $IC_{50}$ was calculated as the concentration required for inhibition of cytokine production in MNCs by 50% relative to the control (treated with SEB only, without compound 4210 treatment) shown in FIG. 2A.

FIGS. 2A and 2B. Inhibition of Pro-Inflammatory Cytokines with Exposure to SEB, LPS or *B. mallei* in Primary Cultures by Compound 4210

PBMCs ($1\times10^6$) from three normal donors were cultured for 20 h with SEB (200 ng/ml) with or without compound 4210 (250 μM to 0.5 μM). The culture supernatants were collected and measured for cytokine by CBA assay. PBMCs ($1\times10^6$) from a normal donor was stimulated with LPS extracted from *F. tularensis* (10 μg) or *E. coli* (1 μg) or irradiated *B. mallei* (10 μg) in the absence or presence of various concentrations of 4210 by MSD assay as described in materials and methods. The data presented as $IC_{50}$, calculated as the concentration required for inhibition of cytokine production in MNCs by 50% relative to the control. (FIG. 2A) $IC_{50}$ to SEB; (FIG. 2B) $IC_{50}$ to LPS extracted from *F. tularensis* or *E. coli* or Irradiated *B. mallei*. Data presented representative of three independent experiments.

FIG. 2C. Pro-Inflammatory Cytokine Inhibition by Compound 1 and Compound 4210 in Primary Culture of PBMCs Stimulated with SEB PBMCs ($1\times10^6$) from two normal donors were cultured for 20 h with SEB (200 ng) with or without compound 1 (500 μM to 1 μM) or compound 4210 (500 μM to 0.01 μM) treatment under the same experimental condition. The culture supernatants were collected and measured for cytokines by MSD assay as described in materials and methods. The data presented as cytokine production (pg/ml)±STD in the absence or presence of compound 1 and compound 4210 of two individual donors (donor 1 and donor 2). The dose dependent inhibition of IFN-γ, IL-1β, and TNF-α by compound 1 and compound 4210 of donor 1 and donor 2 was used to calculate $IC_{50}$ as the concentration required for cytokine inhibition by 50% relative to the control (without inhibitor). $IC_{50}$ of compound 1 and compound 4210 are shown below.

| | Donor 1 $IC_{50}$ [μM] | | | | Donor 2 $IC_{50}$ [μM] | | | |
|---|---|---|---|---|---|---|---|---|
| | IFN-γ | IL-1β | IL-6 | TNF-α | IFN-γ | IL-1β | IL-6 | TNF-α |
| Compound 1 | 41 | 35 | 14 | 19 | 40 | 24 | 35 | 14 |
| Compound 4210 | 0.3 | 0.37 | 0.4 | 0.37 | 0.9 | 0.73 | 0.17 | 0.27 |

FIG. 2D. Pro-Inflammatory Cytokine Inhibition by Compound 4210 in Primary Culture of PBMCs Stimulated with *F. tularensis* or *E. coli* or *B. mallei*

PBMCs ($1\times10^6$) were cultured for 20 h with *F. tularensis* or *E. coli* or *B. mallei* (irradiated, 10 μg) (500 μM to 1 μM)

or compound 4210 (500 µM to 0.01 µM). The culture supernatants were collected and measured for cytokines by MSD assay as described in materials and methods. The data presented as cytokine production (pg/ml)±STD in the absence or presence of compound 4210.

Figure 3A:
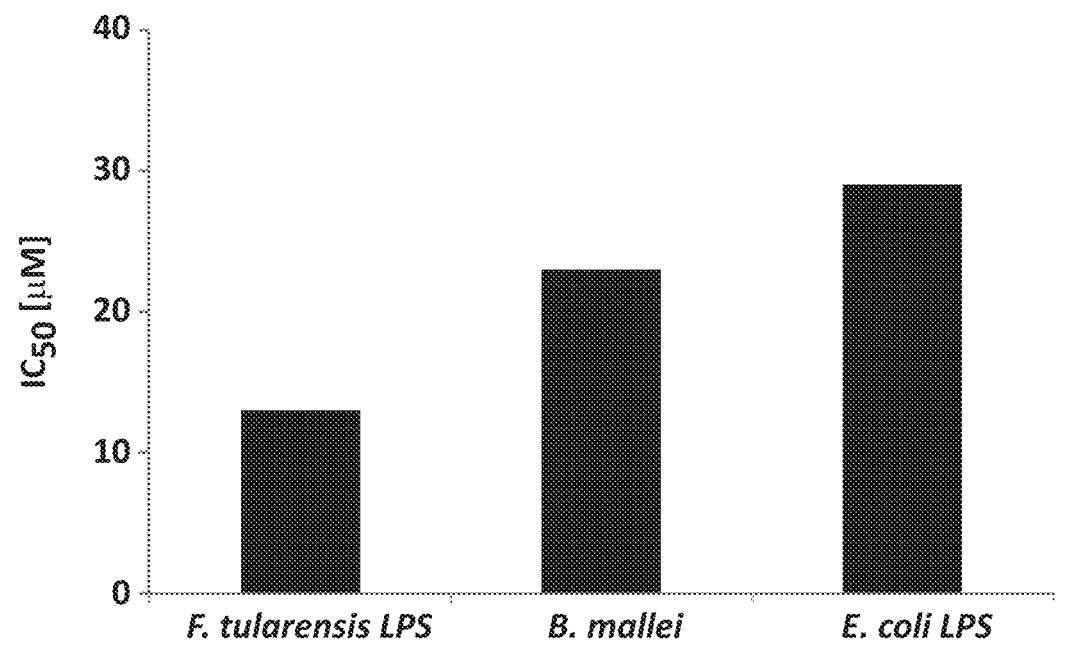

FIG. 3A. MyD88-Specific Signaling Inhibited by Compound 4210

Compound 4210 was tested for MyD88-specific signaling by monitoring LPS-induced SEAP activity by a NF-kB driven signaling pathway for reporter gene expression. HEK 293 stable transfected cell line (TLR4-MD2-NF-kB-SEAP) was stimulated with LPS (TLR-4 ligand) and treated with varying concentrations of compounds 4210(500 µM to 0.01 µM). Culture supernatants were tested for SEAP activity and compared to levels in the absence of compounds (positive control). The data presented as $IC_{50}$, calculated as the concentration required for inhibition of cytokine production in MNCs by 50% relative to the control.

Figure 3B:
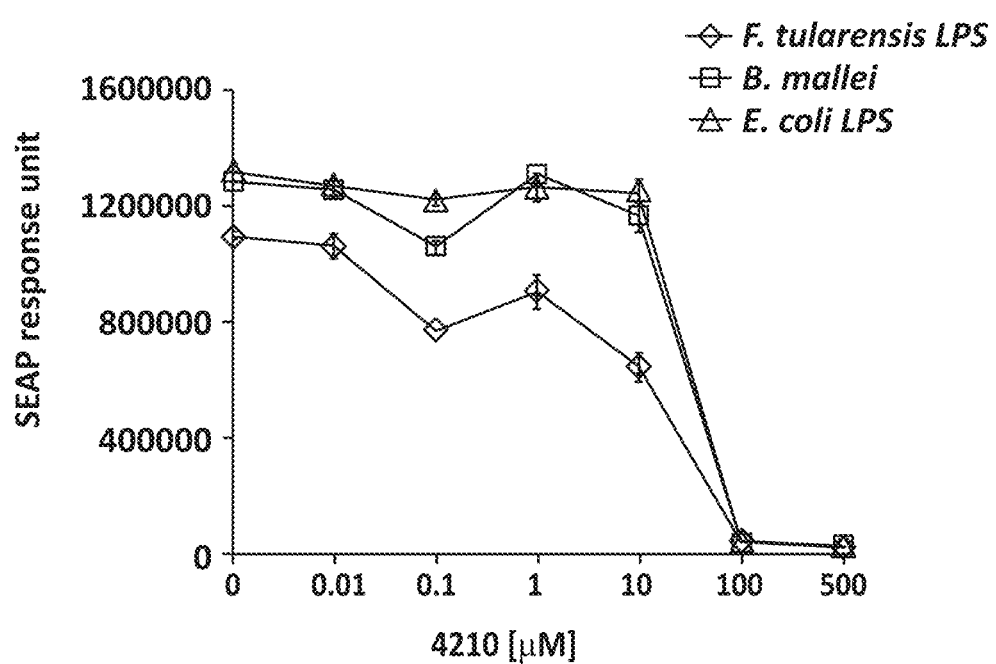
FIG. 3B is a graph showing dose dependent inhibition SEAP expression (inhibition of MyD88-specific signaling of SEAP reporter expression) by compound 4210 in cell culture stimulated with LPS (*F. tularensis* or *E. coli*) or irradiated *B. mallei*.
Figure 4A:
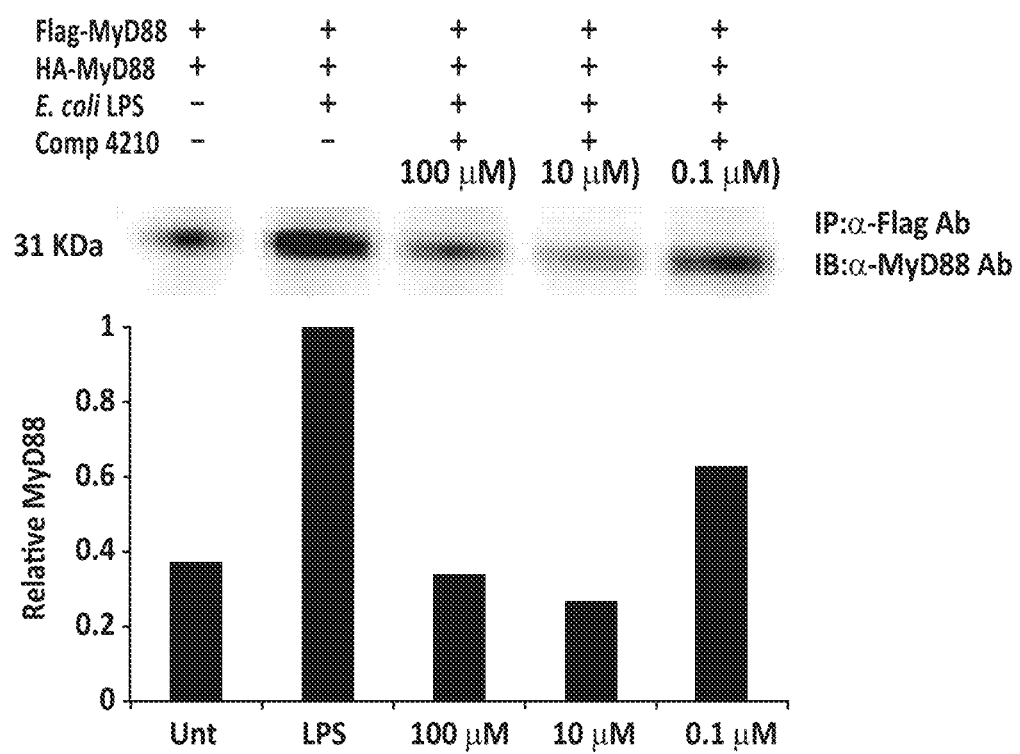
FIG. 4A is a graph showing inhibition of MyD88 homodimer formation from newly expressed MyD88 in the presence of compound 4210 with immunoblot probed with anti-MyD88.
Figure 4B:
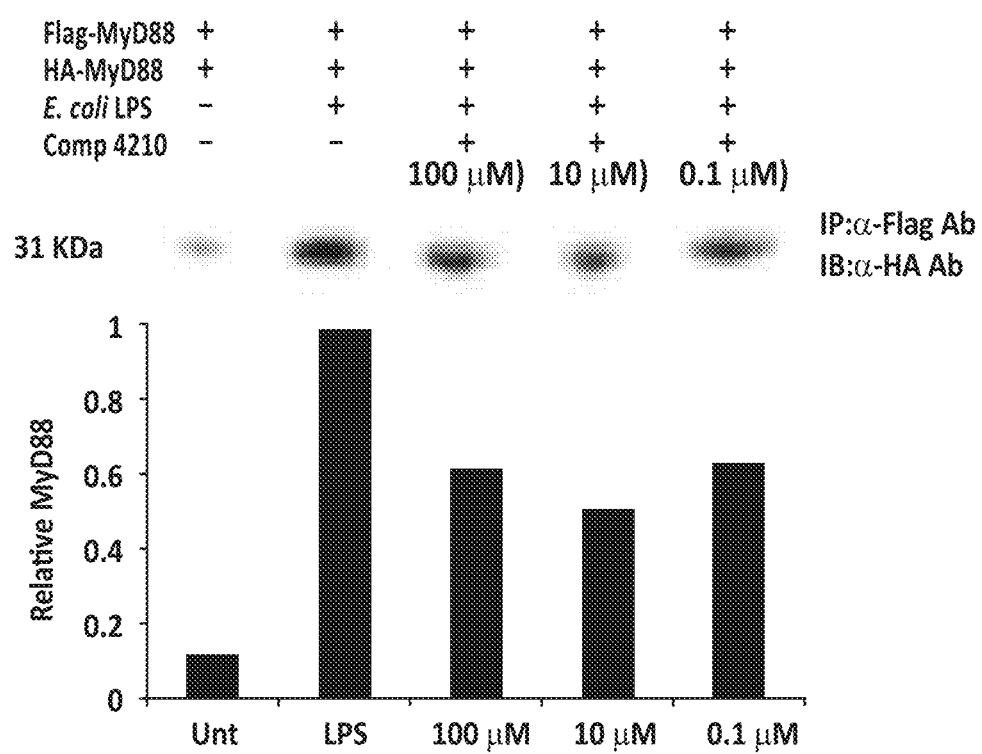
FIG. 4B is a graph showing inhibition of MyD88 homodimer formation from newly expressed MyD88 in the presence of compound 4210 with immunoblot probed with anti-HA antibody.

FIG. 3B. MyD88-Specific Signaling of SEAP Reporter Expression Inhibited by Compound 4210

Compound 4210 tested for MyD88-specific signaling by monitoring SEAP activity by a NF-kB driven signaling pathway for reporter gene expression. HEK 293 stable transfected (TLR4-MD2-NF-kB-SEAP) cells ($5 \times 10^5$ cells/ml) was stimulated with LPS [$F.$ $tularensis$ (10 µg) or $E.$ $coli$ (1 µg) or irradiated $B.$ $mallei$ (10 µg)] in the absence or presence of various concentrations of 4210 (500 µM to 0.01 µM). Culture supernatants were tested for SEAP activity. The data presented as dose dependent inhibition as SEAP response unit±SEM and $IC_{50}$ was calculated as the concentration required for inhibition of SEAP activity by 50% relative to the control (without compound 4210 treatment) shown in FIG. 3.

FIGS. 4A and 4B. Inhibition of MyD88 Homodimer Formation from Newly Expressed MyD88 in the Presence of Compound 4210

HEK 293-SEAP-TLR4 cells were co-transfected with plasmids MyD88-Flag or pCMV-HA-MyD88. Six hours after transfection, cells were incubated for 40 h with or without the compound 4210 (100 μM, 10 μM to 0.1 μM). Cell extracts were immunoprecipitated (IP) with anti-Flag antibody, and immune-precipitated proteins were analyzed in Western blot by probing with anti-MyD88 antibody. The blot was stripped in stripping buffer and then reprobed with anti-HA antibody. Relative level of MyD88 was determined by densitometry. (FIG. 4A) Immunoblot probed with anti-MyD88; (FIG. 4B) Immunoblot with probed with anti-HA antibody. Lower panels represent densitometry analyses of the results shown in (FIG. 4A) and (FIG. 4B). The results presented as representative data of two independent experiments.

FIGS. 5A, 5B and 5C. Cytokine Inhibition by Compound 4210 with Exposure to SEB, LPS or *B. mallei* in Mouse Spleen Cell Cultures Spleen cells ($2\times10^6$)/well from BALB/c, C57BL/6 and $MyD88^{-/-}$ mice were cultured in a 48-well (300 μl/well) plate for 20 h with SEB (200 ng/ml), *E. coli* LPS (1 μg/m) or *B. mallei* (10 μg/ml) with or without 4210 (100 μM to 0.1 μM) treatment 30 min before antigen exposure as indicated in the figures. The culture supernatants were collected and measured for cytokine by MSD assay as described in materials and methods. (FIG. 5A) Cytokine response to *B. mallei* or LPS in C57BL/6 (wild type) and $MyD88^{-/-}$ mice. (FIG. 5B) Cytokine inhibition in spleen cell cultures of BALB/c mice, and (FIG. 5C) C57BL/6 mice in the presence of compound 4210. The data presented in (FIG. 5B) and (FIG. 5C) as $IC_{50}$ concentration. Data presented are representative of three independent experiments.

FIG. 5D. Inhibition of SEAP Reporter Activity by Compound 1 and Compound 4210 Stimulated with LPS (*F. tularensis* or *E. coli*) or *B. mallei*

HEK 293 stable transfected cells (TLR4-MD2-NF-kB-SEAP) was stimulated with LPS (10 μg) extracted from *F. tularensis* or *E. coli,* or irradiated *B. mallei* (10 μg) with or without varying concentrations of 4210 (500 μM to 0.01 μM) or compound 1(500 μM to 1 μM), respectively. Culture supernatants were tested for SEAP activity. Data presented as SEAP response unit±SEM. The dose dependent SEAP inhibition by compound 1 and compound 4210 was used to calculate $IC_{50}$ as the concentration required for inhibition of SEAP expression activity by 50% relative to the control (without inhibitor). $IC_{50}$ of compound 1 stimulated with *F. tularensis* LPS, *E. coli* LPS and *B. mallei* were 87 μM, 180 μM and 270 μM, respectively. $IC_{50}$ of compound 4210 stimulated with *F. tularensis* LPS, *E. coli* LPS and *B. mallei* were 1 μM, 6 μM and 0.47 μM, respectively.

FIG. 6A, 6B and 6C. In Vivo Efficacy of Compound 4210: Attenuation of SEB or LPS-Induced Toxic Shock in Mice.

BALB/c mice (n=6/per group) were injected (i.p.) with different amounts of compound 4210 (0.17 mg, 0.51 mg/ or 1 mg), 30 min later injected with 1 μg of SEB followed by LPS (90 μg, sub lethal dose) 2 h later. Mice were observed to determine if mice survived, or time of death. Control mice injected only with 90 μg of LPS or 1 μg of SEB survived. Data represent three separate experiments. (FIG. 6A) Survivability of mice with pre-treatment of compound 4210; (FIG. 6B) Survivability of mice with post-exposure to SEB; (FIG. 6C) Survivability of mice with pre-treatment of compound 4210 to lethal LPS (120 μg) exposure.

FIG. 6D. Consistent Biological Results (QA/QC) of Different Batches of Compound 4210 Synthesized at Different Times The compound 4210 synthesized at different batches were tested for QA/QC in biological assay for MyD88-inhibitory activity by SEAP reporter assay. Three different batches of the compound 4210 synthesized as described in materials and methods section were tested for LPS-ligand induced SEAP inhibitory effect in HEK 293 stable transfected cells (TLR4-MD2-NF-kB-SEAP) under the same experimental condition. Data presented as the SEAP response unit of cells treated with compound 4210 alone or stimulated with *E. coli* LPS in the absence or presence of varying concentration of compound 4210 (three different batches of 4210). Data presented as SEAP response unit±SEM.

Embodiment 2

In the second embodiment molecule 4210 has been shown to be beneficial in the treatment of most viruses, especially alphaviruses.

Materials and Methods

Reagents

Pooled human AB sera were obtained from Pel-Freez (Brown Deer, Wis. The IFN-β ultra-sensitive cytokine assay kit was purchased from. Primary anti-MyD88 antibody was obtained from AnaSpec, Inc., (San Jose, Calif.) and Alexis Biochemicals (San Diego, Calif.). Anti-β-actin antibody was purchased from Cell Signaling technology (Danvers, Mass.). Plasmid IRF3-HA-MyD88) and plasmid 13093 (MyD88-flag) were purchased through an MTA agreement with Addgene (Cambridge, Mass.). The HEK 293-TLR3 cell line was obtained from In Vivogen. The transfection reagent lipofectamine was purchased from Invitrogen (Carlsbad, Calif.). MyD88 KO HEK293 cell line (HEK293-I3A) was a kind gift from G. Stark (Dept. of Molecular Genetics, Lerner Research Institute, Cleveland Clinic, Ohio). All chemical reagents were purchased from Aldrich and used without further purification. The solvents were purchased from Fisher or J.T. Baker. All deuterated solvents to synthesize 4210 were purchased from Cambridge Isotope Laboratories, Inc. IFN-β (h IFN-β) ELISA kit was purchased from (Piscataway, N.J.). Human glioblastoma astrocytoma cell (ATCC number HTB-14) was purchased from ATCC (Manassas, Va.). Human U87 cells, Vero cells, were obtained from USAMRIID (virology division). MyD88 KO HEK293 cell line (HEK293-I3A) was a kind gift from G. Stark (Dept. of Molecular Genetics, Lerner Research Institute, Cleveland Clinic, Ohio).

Synthesis of 4210:

The MyD88 inhibitor, compound 4210 was synthesized as described above.

Cell Culture and Transfections

One day before transfection, the human TLR3/NF-kB/SEAPorter HEK 293 cells ($1\times10^6$ cells/ml) were cultured in 6 well plate containing DMEM, supplemented with 2.5% FBS (Invitrogen, Carlsbad, Calif.), Sodium Pyruvate (1 mM), L-Glutamine (4 mM), Penicillin-Streptomycin (1%), Blasticidine (10 µg/ml), G418 (500 µg/ml) and grown in a 37° C. humidified atmosphere of 5% $CO_2$. The cells were transfected with 4 µg of Flag-MyD88 plasmid DNA with Lipofectamine 2000 (Invitrogen) method according to the manufacturer's instructions. Compounds (500 µM to 1 µM) followed by E. coli LPS at 1 µg/ml were added to the medium 6 h after transfection. Forty hours post-transfection, cells were collected into fresh 1.5 ml centrifuge tubes and chilled on ice for 5 min before centrifuging. Membrane and cytoplasm were separated by re-suspending the pellets in 50 µl of lysis buffer (Active Motif) in the presence of DTT, protease inhibitors and phosphatase inhibitors on ice for 30-60 min. The membrane fraction was collected by centrifuging lysates at 14,000×g for 20 min. Supernatant contained the cytoplasmic fraction and pellet contained membrane fraction. Samples containing 10 µg of total cytoplasmic proteins separated by SDS PAGE and transferred to nitrocellulose membranes. Nitrocellulose membranes were blocked overnight in Tris-buffered saline containing 0.1% Tween 20 and 3% BSA at 4° C. Blots were extensively washed and probed with a desired monoclonal or antibody polyclonal antibody followed by HRP-conjugated secondary Ab. Blots were washed extensively and developed with chemiluminescent substrate in the presence of hydrogen peroxide using Immun-Star WesternC Chemiluminescent kit (Bio-Rad). An imaging system VersaDoc Model 4000 (Bio-Rad) was used to capture the image.

Co-Transfection and Immunoprecipitation Assay

HEK293T cells (transfected or Mock) were collected 48 h after transfection, washed with 2 ml of ice-cold PBS, and lysed in 80 µl of buffer [50 mM HEPES, pH7.4]. Cells were pelleted by centrifugation at 10,000×g for 10 min at 4° C., and cytosolic fractions were collected for immunoprecipitation. Cell extracts (1 mg total proteins) were incubated with 2 µg of mouse anti-Flag M2 conjugated with agarose attached to magnetic beads (Sigma-Aldrich) or HA-conjugated agarose beads for 16 h under constant shaking at 4° C. Agarose bead-bound immunocomplexes were separated by a magnetic separator, washed three times, and eluted in SDS-PAGE sample buffer used for co-masse blue staining to cut appropriate band for LC/MS or western blot analysis.

Western Blot Analysis

The transfected cells were chilled on ice for 5 min before being pelleted into fresh 1.5 ml centrifuge tubes. Membrane and cytoplasm separation was done by suspending the pellets in 50 µl of lysis buffer (Active Motif) in the presence of DTT, protease inhibitors and phosphatase inhibitors and incubated on ice for 30-60 min. The membrane fraction was collected by centrifuging the lysates at 14000×g for 20 min. The supernatant contained the cytoplasmic fraction. Samples containing 10 µg of total cytoplasmic proteins were separated by gel electrophoresis and transferred to nitrocellulose membranes. The membranes were blocked overnight in 1×Tris-buffered saline (TBS) containing 0.1% Tween-20 and 3% bovine serum albumin at 4° C. The membranes were washed extensively with 1×TBS buffer and then probed with anti-MyD88 polyclonal antibody followed by horseradish peroxidase-conjugated secondary antibody (goat anti-rabbit). After additional rinsing with 1×TBS buffer, the membranes were exposed to a chemiluminescent substrate in the presence of hydrogen peroxide, using Immun-Star Western C Chemiluminescent kit (BioRad). A VersaDoc Model 4000 (BioRad) imaging system was used to capture the image.

Human IFN-β Assay

IFN-β(h IFN-β,) ELISA (kit (VeriKine™ Human IFN-β ELISA Kit, PBL Interferon source, Piscataway, N.J.) was used to measure IFN-β in the culture supernatant by a sandwich immunoassay technique, according to the manufacturers' protocol. Human IFN-β standards and culture supernatants (100 µl) were added to the pre-coated wells containing polyclonal antibody to h-IFN-β and incubated for 1 hr. After washing 3×, the enzyme (HRP)-labeled anti-h IFN-β monoclonal antibody (100 µl) was added to form an antibody-antigen complex where the h IFN-β is sandwiched between the primary and the enzyme-labeled secondary antibody. After 1 h, a color developer substrate (TMB, 100 µl) was used to activate the enzyme reaction. After 15 min incubation of TMB, stop solution was added to each well and the plate absorbance was read in a spectrophotometer at 450 nm. The amount IFN-β was determined from the plot of standard curve of human IFN-β standards.

RANTES Assay

The human RANTES (Regulated upon Activation, Normal T cell Expressed and presumably Secreted) in cell culture supernatants were measured by a quantitative sandwich enzyme immune-assay ELISA (R & D System, Minneapolis, Minn.) according to the manufacturers' protocol. Standards and culture supernatants (100 µl) were added to the pre-coated wells containing monoclonal antibody specific to h-RANTES. After washing 3×, the enzyme (HRP)-labeled antibody conjugate (200 µl) was added to form an antibody-antigen complex. After 1 h (room temperature), a substrate solution (200 µl) was used to activate the enzyme reaction. After 20 min incubation stop solution (50 µl) was added to each well and the plate absorbance was read in a spectrophotometer at 450 nm. The amount RANTES was determined from the plot of standard curve.

Viral Infection and Plaque Reduction Assay

Viral replication in ex vivo cell culture based assay was performed with infection. U87 or Vero cells were infected at a multiplicity of infection (MOI) equal to 10 with VEE Trinidad virus and EEEV for 1 h, cell monolayers were washed twice with medium to remove residual virus, added complete medium containing 4210 or 4211 compound (33 µM to 3 µM). Cells were incubated for 24 hrs and supernatants were harvested for IFN-β assay and virus measured by standard plaque assay.

Mice

The C3H/HeN mice were purchased from Charles River Laboratories (Wilmington, Mass.). All studies were carried out in BSL-3 and were approved by the Institutional Animal Care and Use Committee (IACUC) at the USAMRIID
In Vivo Efficacy Studies of 4210 Against VEEV Challenge Initially, we assessed potential toxicity of 4210 at up to 1 mg/mouse. Intranasal administration of the vaccine strain of VEEV, TC-83, in C3H/HeN mice closely mimics virulent VEEV encephalitis in murine models and has been used as a model to evaluate antivirals for alphavirus infection (Julander J G et al., 2008, Antiviral Research 78, 230-41; Julander J G et al., 2008 Antiviral Research 80; 309-15; Taylor K et al., 2012 30, 4095-4105; Chung, D-H et al., 2014, PLoS Pathogens, 10 e1004213). For antiviral efficacy, ten six to eight week old C3H/HeN mice were randomly assigned to one of four treatment groups: Group 1—Compound 4210 0.5 mg/mouse, Group 2—0.25 mg/mouse, Group 3—Vehicle control (diluent) and Group 4—untreated. Treatments were conducted for five days, beginning 2 hours prior to virus challenge. Mice were infected with intranasal (i.n.) inoculation with vaccine strain of VEEV (TC-83) ($1 \times 10^5$ pfu) (day 0) diluted in 20 µl of PBS. For vehicle control, DMSO in PBS was used. Mice were weighed from D0-D14 and checked twice a day for mortality and morbidity.

Embodiment 2 Results
LPS Stimulation of U937 Cells in the Presence of a MyD88 Inhibitor Compound 4210 Enhanced IFN-β Production.

Figure 7A:
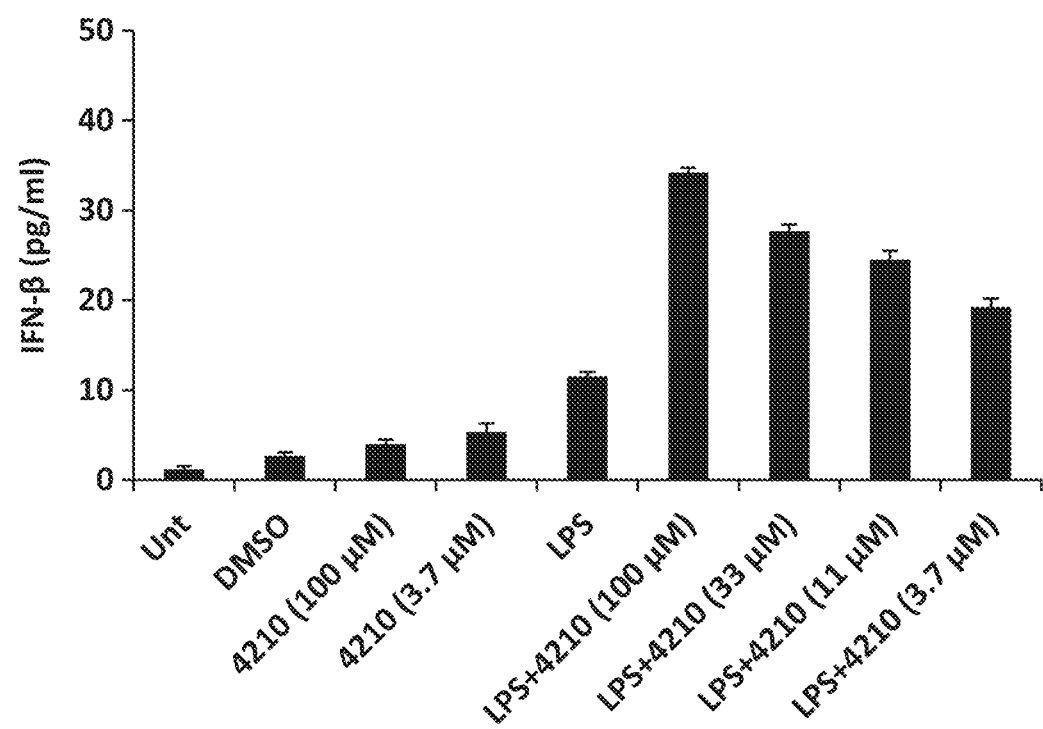
FIG. 7A is a graph showing an induction of IFN-β production in the presence of compound 4210 upon LPS stimulation of U937 cells.
Figure 7B:
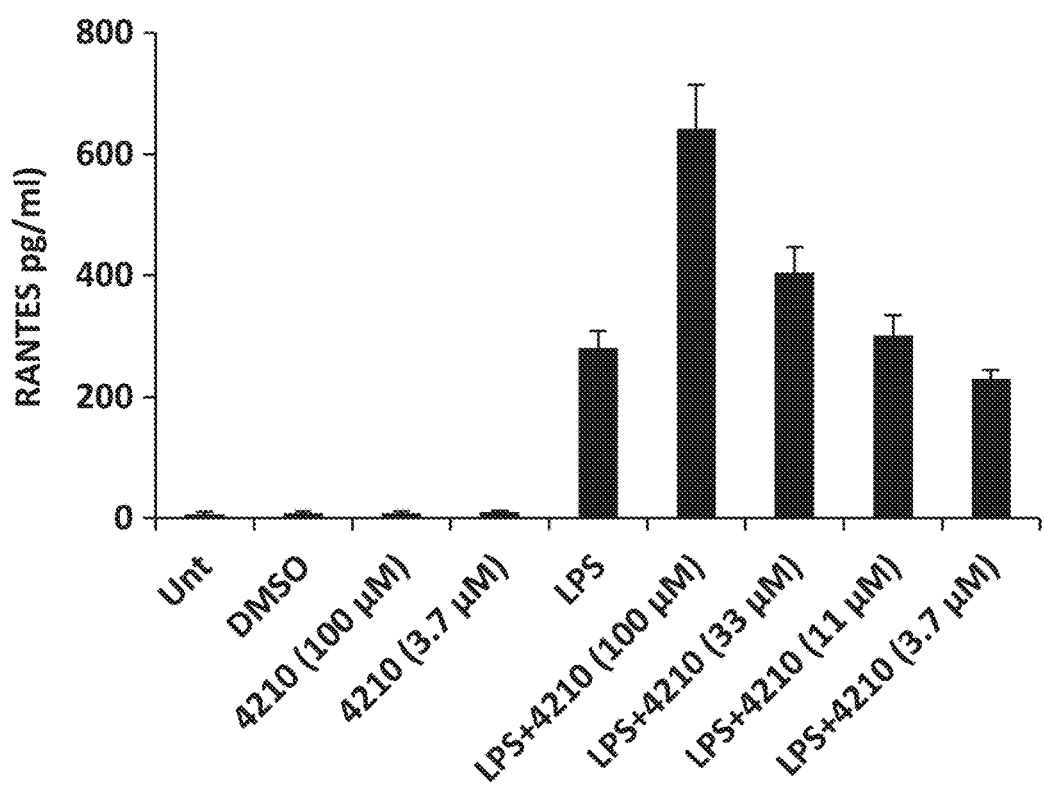
FIG. 7B is a graph showing an induction of RANTES production in the presence of compound 4210 upon LPS stimulation of U937 cells.

Monocytes/macrophages respond to bacterial lipopolysaccharide (LPS) via MyD88 dependent and independent (TRIF-dependent) pathway. Type I IFN is generally induced by LPS (TLR4 ligand), double stranded RNA (TLR3 ligand) and viral infections (Kawai, T et. al, 2001 J. Immunol 167, 5887-5894; Hemmi, H et al., 2004, J. exp. Med. 199,1641-1650; Hoshhino, K et al., 2002, Int. Immunol, 14 1225-1231) wherein IRF3/IRF7 plays a crucial role in the primary activation of IFN-β. MyD88 deficiency has been reported to increase IFN-β production upon poly I: C or virus infection (Siednienko J. et al., 2010, J. Eur. Immunol. 40:3150-3160; 2011, J. Immunol. 186:2514-2522). In light of these reports we first examined whether LPS-induced MyD88 inhibition in human monocytic U937 cells by MyD88 inhibitor compound 4210 would increase antiviral IFN-β and RANTES production. The results showed a dose dependent increase in IFN-β production by U937 cells (over 3 fold increased at 100 µM concentration) when stimulated with LPS in the presence of a MyD88 inhibitor compound 4210 compared to without treatment (FIG. 7A). Along with IFN-β, we also observed an increase in antiviral RANTES production by U937 cells in the presence of compound 4210 (FIG. 7B). Studies have shown that MyD88 -dependent or MyD88-independent pathway induces co-stimulatory molecules (S. Akira and K Takeda, C. R. Biologics 327 (2004). LPS stimulation is known to up regulate co-stimulatory molecules following MyD88 independent pathway production of IFN-β, which are secondary to IFN-β. We also noticed an increase of CD86 and CD80 expression upon LPS stimulation of U937 cells in the presence of MyD88 inhibitor (data not shown). These results suggest that MyD88 inhibition induced IFN-β via MyD88-independent pathway. As an initial test, these results prompt us to follow MyD88 independent TLR3-dependent induction of IFN-β in the presence of MyD88 inhibitor compound 4210 in a virus like infection such as poly I: C stimulation.

TLR3-Dependent Induction of IFN-β by Compound 4210 Treatment

Figure 8A:
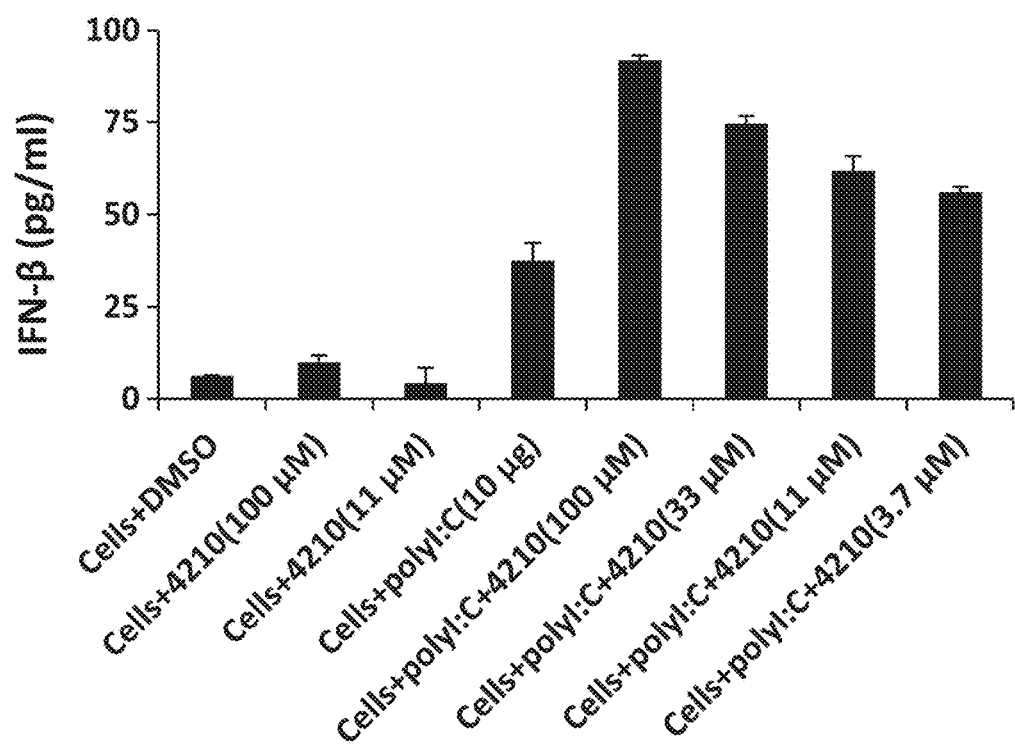
FIG. 8A is a graph showing TLR3-dependent induction of IFN-β with compound 4210 treatment.
Figure 8B:
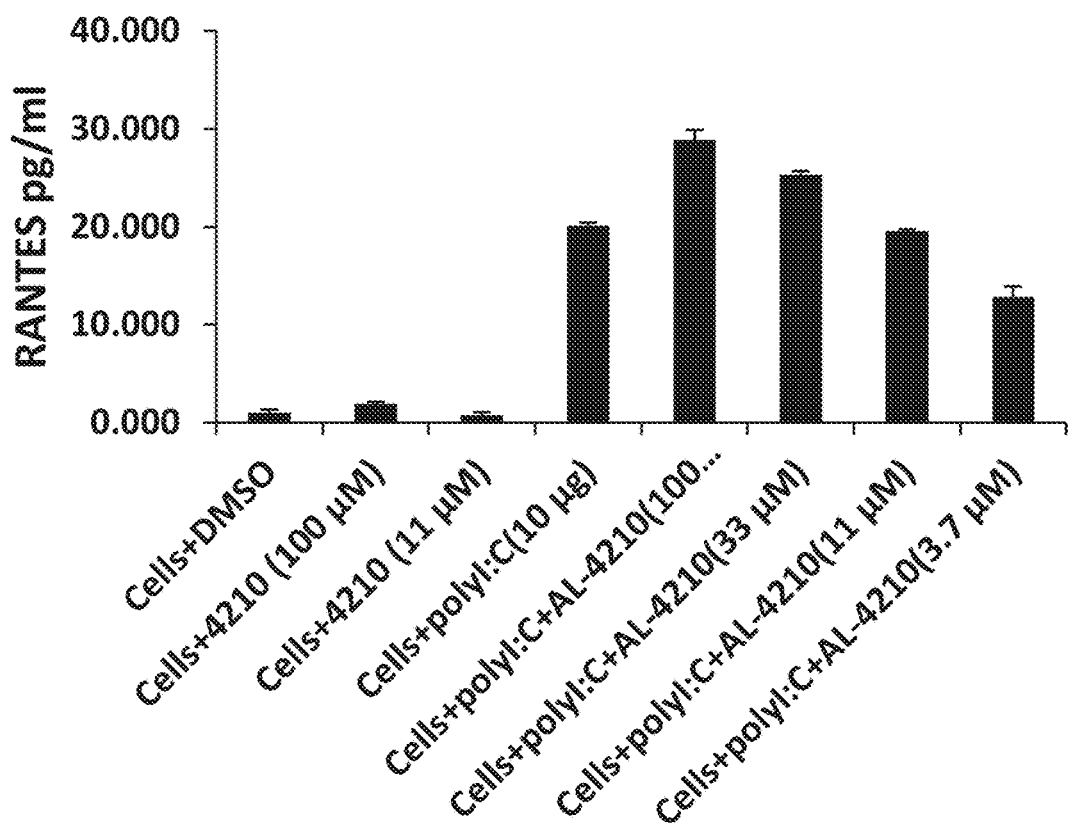
FIG. 8B is a graph showing TLR3-dependent induction of RANTES with compound 4210 treatment.
Figure 8C:
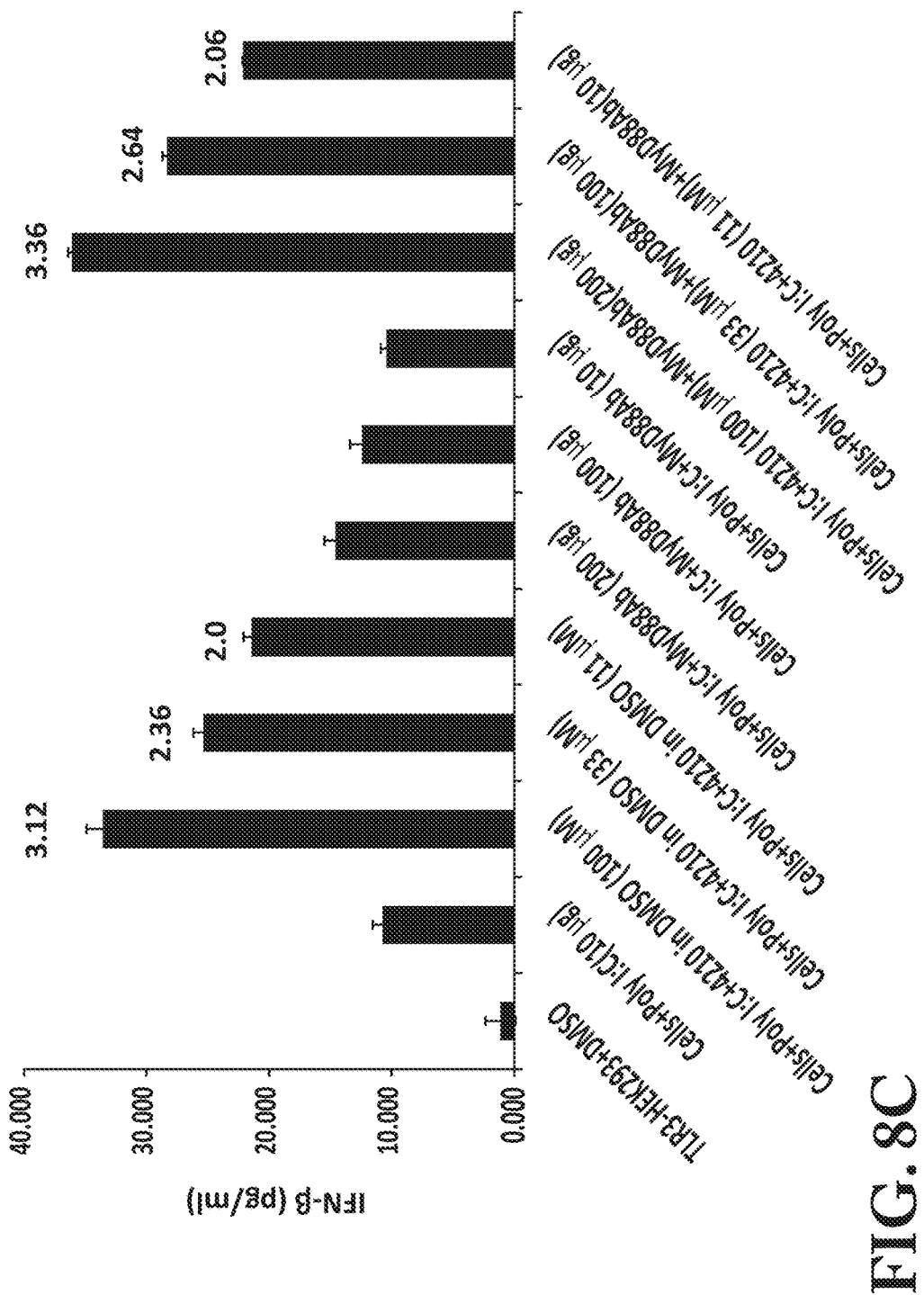
FIG. 8C is a graph showing TLR3-dependent IFN-β was induced by MyD88 inhibitor 4210, an intracellular effect on MyD88 and not by MyD88 antibody.

To test whether MyD88 inhibition by compound 4210 would allow TLR3-dependent increase in IFN-β induction, we used TLR3 transfected a stable cell line HEK293-TLR3 and stimulated with poly I: C. Over 3 fold increase in IFN-β production was observed with poly I: C stimulation in the presence of compound 4210 at 100 µM concentration and dose dependent induction of IFN-β compared to cells that were not treated with MyD88 inhibitor (FIG. 8A). Compound 4210 treatment also increased in RANTES production (FIG. 8B). In addition, we also observed that anti-MyD88 antibody treatment did not induce IFN-β production whereas 4210 treatment induced 3 fold increase in IFN-β production indicates an intracellular effect of the compound 4210 on MyD88 (FIG. 8C). These results suggest that MyD88 inhibition by compound 4210 increased IFN-β production initiated upon TLR3 engagement likely via TLR3-TRIF immune signaling pathway.
Poly I: C Stimulation of Human Glioblastoma Astrocytoma U87 Cells in the Presence of 4210 Augmented IFN-β and RANTES Production.

Figure 9A:
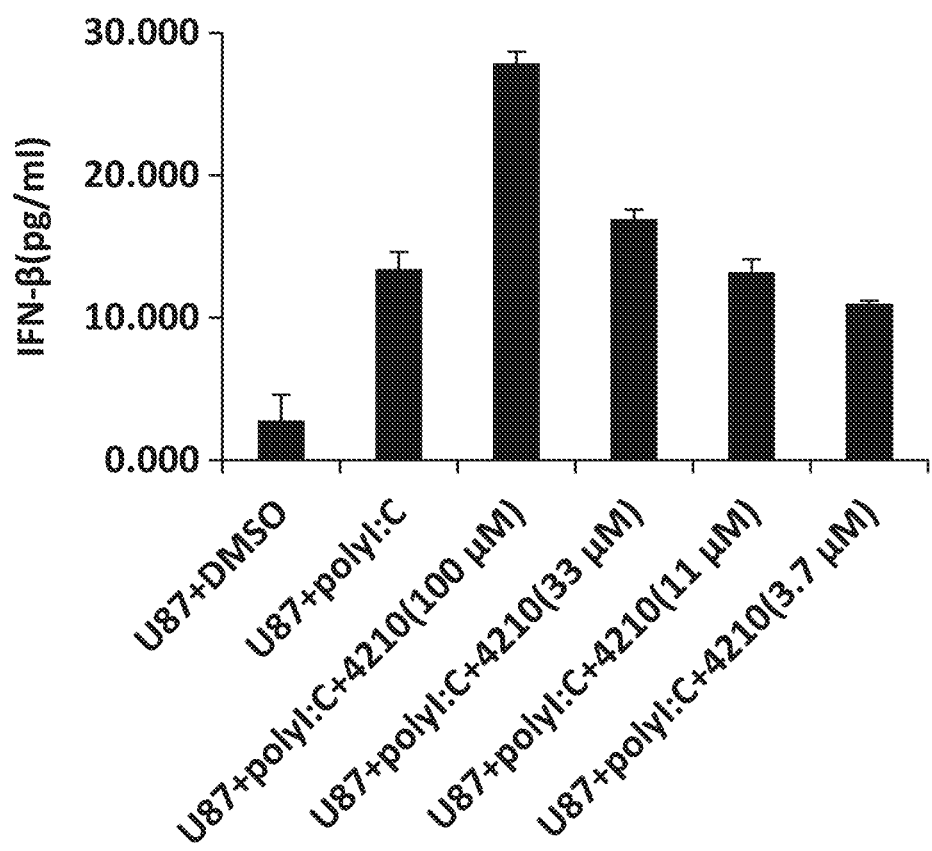
FIG. 9A is a graph showing Poly I: C stimulation of U87 cells in the presence of 4210 increased INF-β production.
Figure 9B:
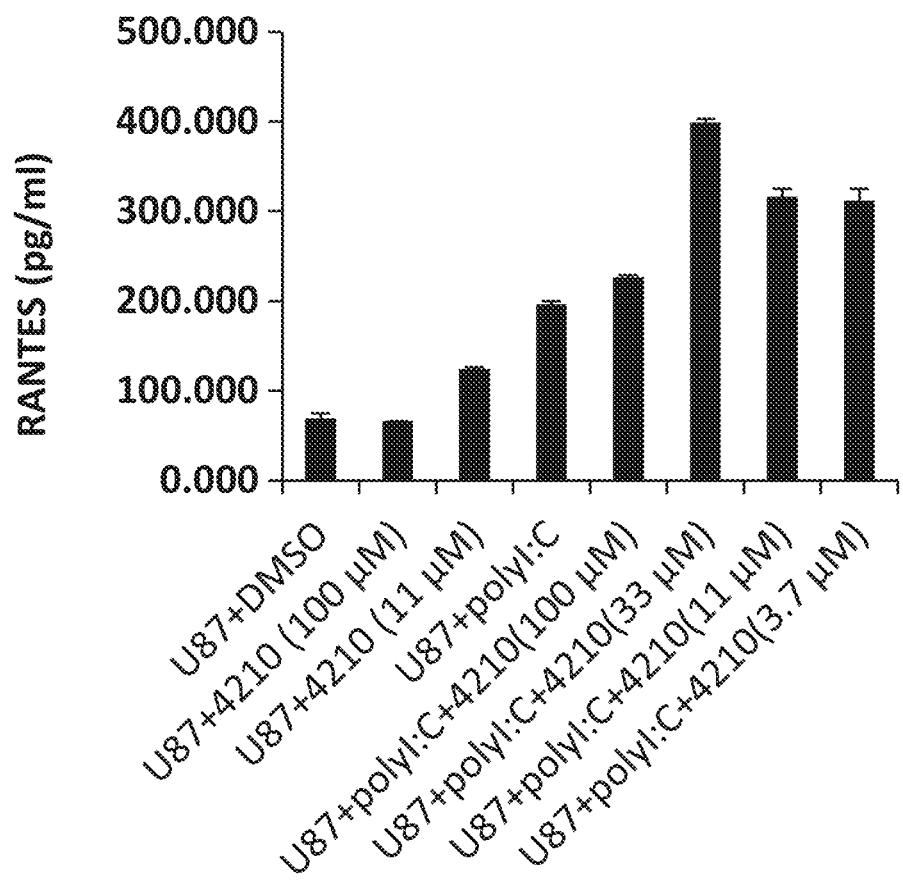
FIG. 9B is a graph showing Poly I: C stimulation of U87 cells in the presence of 4210 increased RANTES production.
Figure 10A:
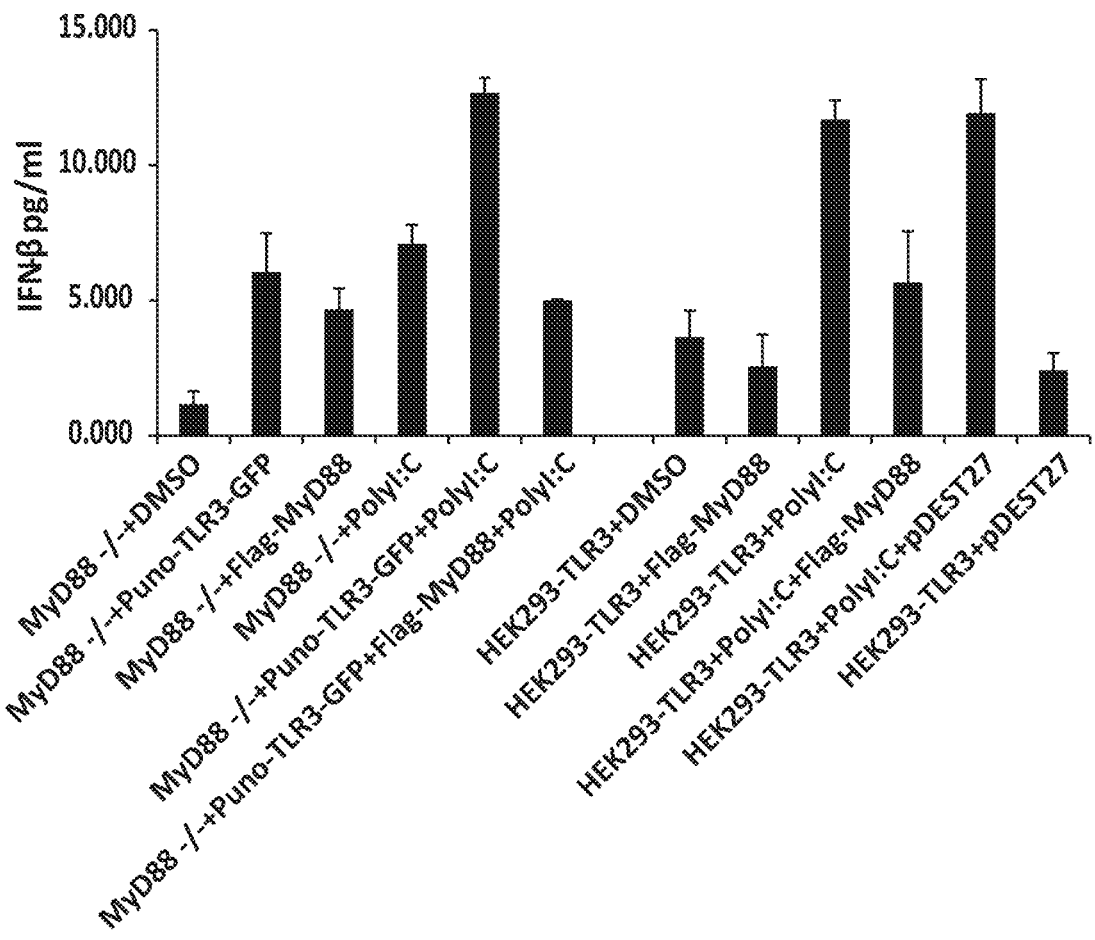
FIG. 10A is a graph showing MyD88/-deficiency augmented IFN-β production and over expression of MyD88 inhibited IFN-β production upon stimulation with poly I:C.
Figure 10B:
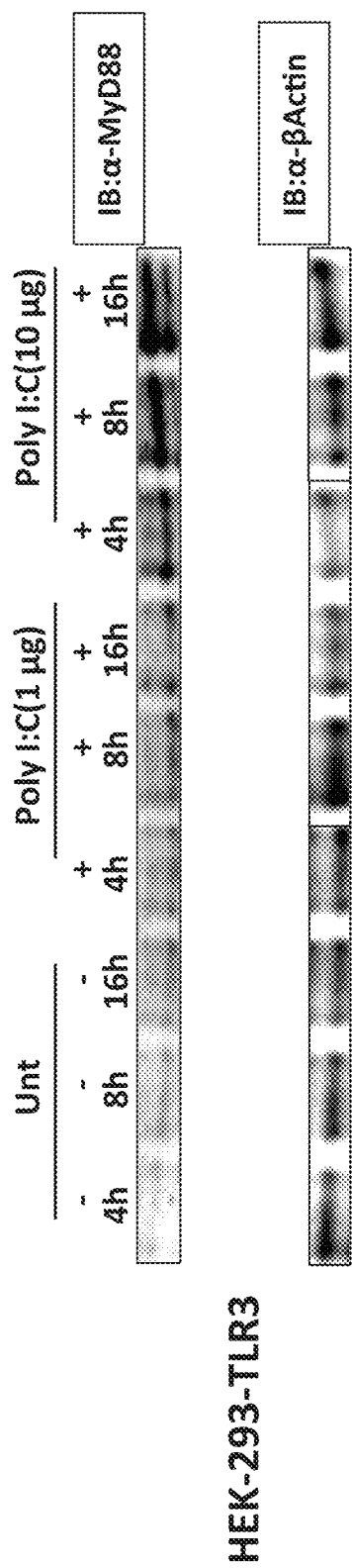
FIG. 10B is a digital photograph of an immuloblot analysis of MyD88 up regulation after poly I: C stimulation of HEK293-TLR3 cells at 4 hours, 8 hours and 16 hours.

Type I IFNs (IFNα/β) are generally produced by almost every cell type, such as leucocytes, fibroblasts, endothelial including neuronal cells upon virus infections. Alpha virus infections cause efficient and rapid spread of virus throughout the neurons of the central nervous system (CNS) resulting in pathogenesis and death of neural cells. IFN evasion is likely an important determinant of VEEV and other alpha virus dissemination and cause disease within the hosts As an initial step to examine whether the inhibition of MyD88 would up regulate antiviral IFN-β in a virus like-infection, we tested human U87 cells with poly I: C stimulation in the presence of compound 4210 and examined IFN-β and RANTES release in culture supernatant. Results shown in FIG. 9A indicate that treatment of MyD88 inhibitor 4210 increased IFN-β production in a dose dependent manner. Similarly an increase in RANTES production in U87 was also observed with 4210 treatment (FIG. 9B). These results suggest that similar to virus like infections inhibition of MyD88 up regulation increased IFN-β production.
Over Expression of MyD88 Inhibited IFN-β Production Earlier reports indicate that following VEEV infection a significant up regulation of signaling molecules including MyD88 was resulted in the mouse brains (Sharma A et al., 2009). It is also reported that Coxsackie virus B3 infected mice the levels of cardiac expression of MyD88 was increased quickly and persisted even beyond day 10 and MyD88$^{-/-}$ mice showed significantly low mortality rates compared with MyD88$^{+/+}$ mice and IFN-β production was significantly increased in MyD88$^{-/-}$ mice (Fuse, K et al., 2005) which indicate MyD88 over expression likely negatively influences antiviral IFN-β production during viral infection. To further extend our observation that over expression of MyD88 reduced IFN-β production, we transfected HEK293-TLR3 cells with a plasmid expressing MyD88 (Flag-MyD88) or a control plasmid (pDEST27) followed by poly I: C stimulation. Results shown in FIG. 10A indicated that indeed over expression of MyD88, reduced poly I: C-induced IFN-β production in the culture supernatant and no effect of a control plasmid transfection. Similar results were observed with MyD88 deficient cell line. MyD88 knock out HEK293 cells co-transfected with Puno-TLR3 plasmid and Flag-MyD88 followed by Poly I: C stimulation demonstrated that over expression of MyD88 reduced IFN-β production compared to (Flag-MyD88) non-transfected HEK293 cells stimulated with poly I: C (FIG. 10A). To validate further that HEK293-TLR3 cells as a consequence of poly I: C stimulation induced MyD88, we examined for MyD88 after treating with different concentration poly I: C. Our results showed that indeed after poly I: C stimulation MyD88 was up regulated (FIG. 10B). These results in agreement with the earlier reports suggest that similar to virus like infection MyD88 is up regulated (Sharma A et al., 2009) and this up regulation of MyD88 may negatively contribute in the production of IFN-β (Siednienko, Jet al., 2010, 2011). Thus, these results suggest that TLR3 dependent induction of IFN-β in a virus-like infection was inhibited by MyD88 and treatment with inhibitor of MyD88 increased IFN-β production. Similar up regulation of MyD88 was observed with U87 cells when stimulated with poly I: C (data not shown).

Figure 11:
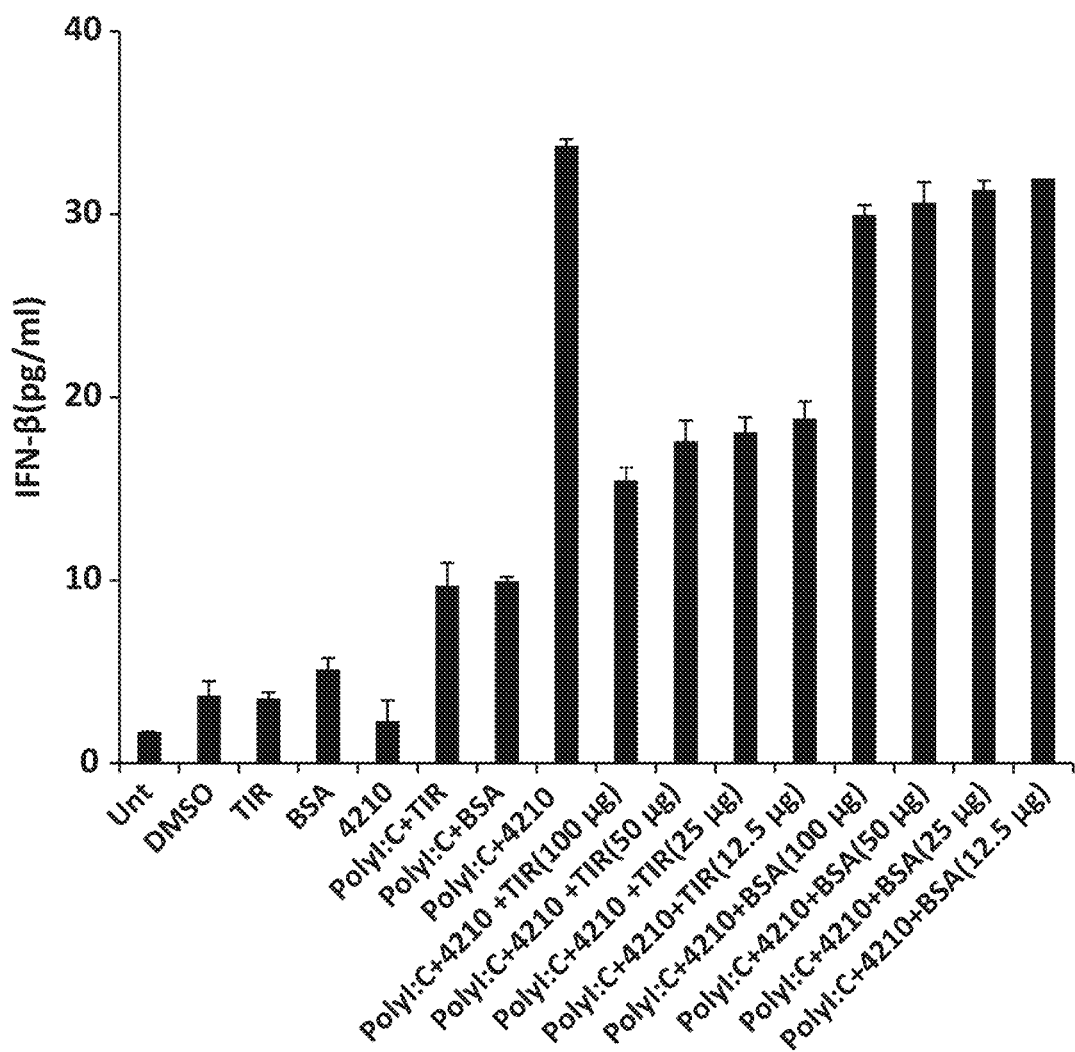
FIG. 11 is a graph showing Stimulation of HEK293-TRL3 cell with poly I: C in the presence of compound 4210 (100 μM) pre-incubated with different dose of recombinant TIR domain of MyD88 protein reduced IFN-β production.

Pre-Adsorption of Compound 4210 with Recombinant TIR Domain of MyD88 Protein Reduced IFN-β Production To further validate that MyD88 up regulation negatively contributing in the induction of antiviral immunity, and the treatment of with compound 4210 functionally contributing to IFN-β induction, we examined whether pre-adsorption of 4210 with recombinant TIR domain protein of MyD88 which binds to the TIR domain of MyD88 would reduce IFN-β production upon stimulation with poly I: C. In our earlier reports we described that MyD88 inhibitor 4210 binds specifically to TIR domain of MyD88 (Kissner et al. 2012). For this, we stimulated HEK293-TLR3 cells with poly I: C in the presence of compound 4210 pre-adsorbed with TIR domain protein and measured IFN-β and RANTES production in culture supernatant. Results shown in FIG. 11 demonstrate that pre-adsorption of compound 4210 (100 μM) with different concentration of TIR domain protein decreased IFN-β production in a dose dependent manner compared to compound 4210 without pre-absorption. As non-specific control pre-adsorption of 4210 with BSA did not reduce IFN-β production (FIG. 11). These results suggest that 4210 binding to TIR domain of MyD88 during pre-absorption reduced inhibitory activity of 4210, thereby, reduced IFN-β production. The specificity of 4210 interaction with MyD88 was also confirmed by a ligand induced cell based reporter assay where compound 4210 treatment inhibited MyD88-mediated signaling of SEAP reporter gene expression described elsewhere (Alam et al., 2014). These results suggest that binding of 4210 with MyD88 limited MyD88 availability for negative effect, thus, annulment of negative effect allowed increased production of IFN-β.

Figure 12:
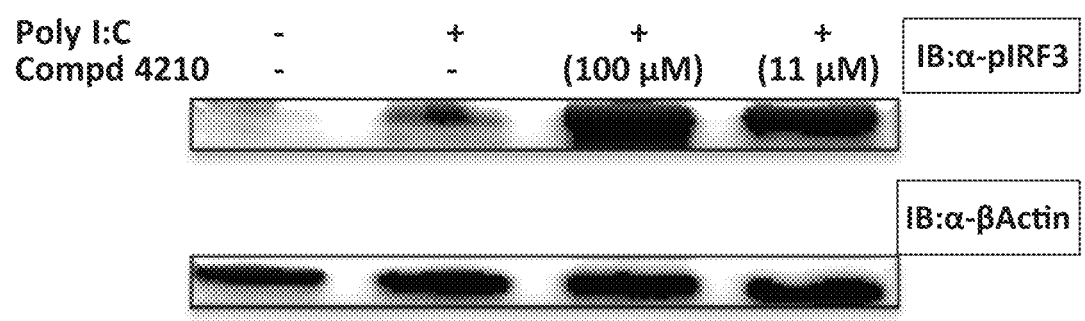
FIG. 12 is a digital image showing compound 4210 increased phosphorylation of IRF3 in HEK293-TLR3 cells stimulated with poly I:C.

Induction of IFN-β Production Correlates with Up Regulation of IRF3 Phosphorylation Of the currently known members of the IRF family in mammals, IRF3 and IRF7 seem to be most critically involved in virus-induced IFN responses (Honda, K and Taniguchi, T. 2006, Nat. Rev. Immunol. 6, 644-658). It has been demonstrated that IRF3 is phosphorylated by TANK-binding kinase-1 and IkB kinase-e in a TRIF-mediated signaling cascades downstream of TLR3/4 (Fitzgerald, K. A. et al., 2003, Nat. Immunol. 4:491-496). IRF-3 is expressed constitutively in a variety of cells and localizes in the cytoplasm as an inactive monomer (Wathelet, M. G., et al 1998, Mol. Cell 1:507; Lin, R. et al, 1998, Mol. Cell. biol 18:2986; Servant, M. J., et al., 2002, Biochem. Pharmacol.64:985; Sato, M. et al., 1998, FEBS Lett. 425:112). IRF3 has potential virus-mediated phosphorylation sites in the C-terminal region (Ser385, 386, 396,398,402,405, and Thr404 of human IRF-3). Phosphorylation of ser396 was first reported by using phosphor-specific antibody (Servant, M. J., et al. 2003, J. Biol. Chem. 278:9441). As an initial test of MyD88 involvement negatively influencing the induction of IFN-β production via IRF pathway, we examined up regulation of IRF3 phosphorylation using anti-phospho IRF-3 (Ser96) antibody with poly I: C stimulation in the presence of compound 4210 to correlate the mediation of IFN-β production. We observed an increase in phosphorylation of IRF-3 with poly I: C stimulation in HEK293-TLR3 cells and increase in phosphorylation was observed in a dose dependent manner in the presence of MyD88 inhibitory compound 4210 (FIG. 12). These results suggest that increase in IFN-β induction is consistent with increased phosphorylation of IRF3 in the presence of MyD88 inhibitor 4210 via TLR3-TRIF-IRF3/IRF7 pathway.

Figure 13:
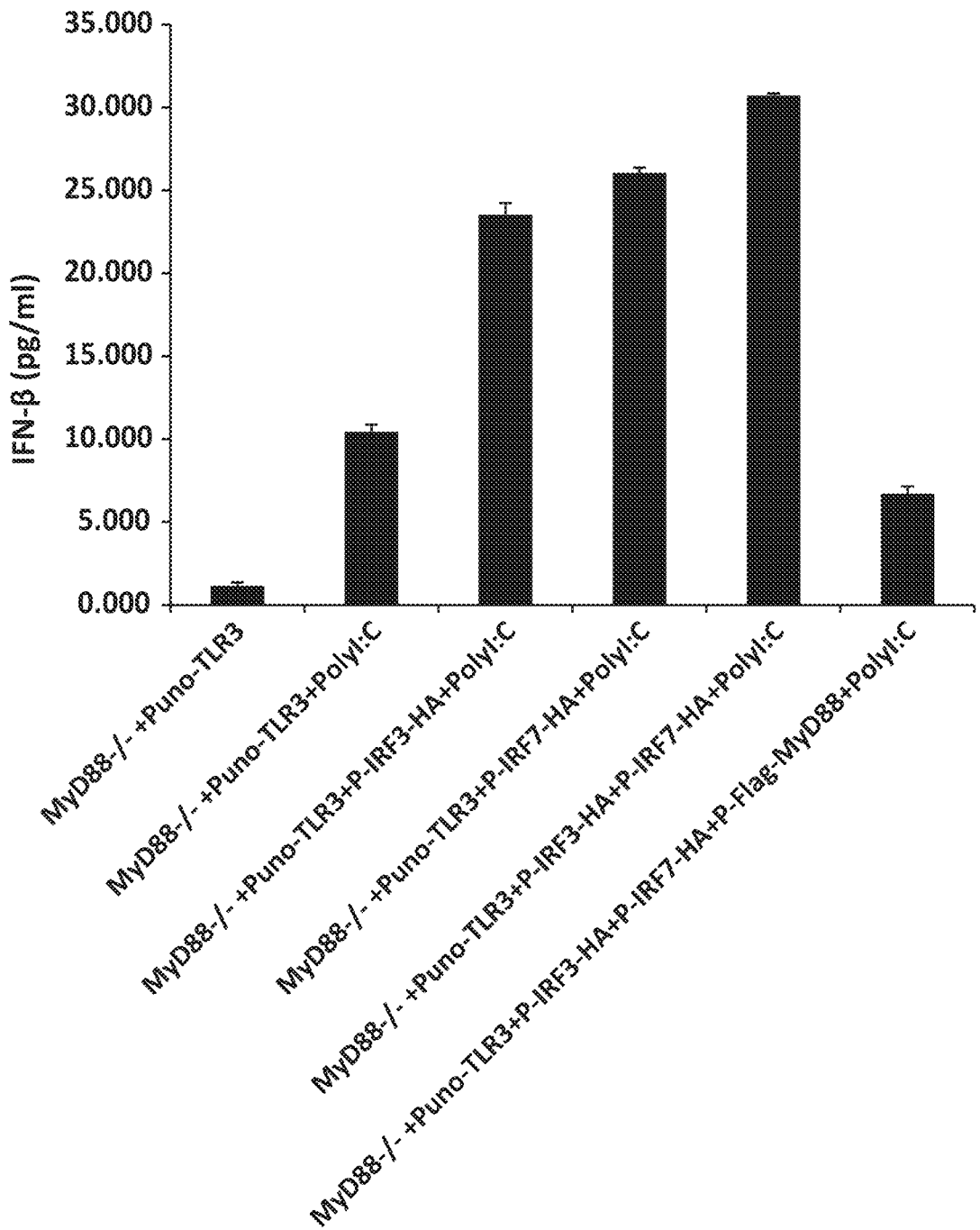
FIG. 13 is a graph showing over expression of IRF3 and/or IRF7 in MyD88 deficiency increased TLR3-dependent IFN-β induction and over expression of MyD88 decreased IFN-β production.

Co-Expression of IRF3/IRF7 in MyD88−/− Cells Increased IFN-β Production and MyD88 Expression Decreased IFN-β Production IRF3 and IRF7 are downstream effectors of PRR/PAMP interactions that lead to IFN β/α expression. Although it is known that a number of viruses make a disruptive effort to disable IRF3/7-activated antiviral pathways of IFN-β production, sequestration of molecules such as IRF3 and IRF7 in the IFN circuit by host cell factor has not been clearly delineated. To confirm that increase in intracellular MyD88 up regulation with virus like infection (Poly I: C stimulation) sequester IRF3/IRF7 and thereby limit IFN production, we transiently expressed IRF3/IRF7 in the presence and absence of MyD88 expression. For this we used MyD88−/− cells such as HEK 293-I3A cells that were transfected with either plasmid Puno-TLR3-GFP, Puno-TLR3-GFP and plasmid P-IRF3-HA, or Puno-TLR3-GFP and plasmid P-IRF7-HA, or Puno-TLR3-GFP, plasmid P-IRF3-HA, plasmid P-IRF7-HA and Flag-MyD88. Results shown in FIG. 13 clearly demonstrate that while IRF3 or IRF7 or IRF3 and IRF7 together increased IFN-β production in the absence of MyD88, in contrast, overexpression of MyD88 reduced poly I: C induced IFN-β production. Similar to earlier results in FIG. 10A and 10B, we also observed that co-expression of MyD88 and IRF3/IRF7 in HEK293 MyD88−/− cell line reduced IFN-β production. These results demonstrate that during virus-like infection MyD88 is up regulated and this MyD88 up regulation sequesters IRF3/IRF7 through interaction, thereby curtails availability of IRFs and limit IRF-mediated signaling and impairs IFN-β production.

Interaction of MyD88 with IRF3 /IRF7

RIG-I or TLR3 recognition of viruses or poly I: C initiate MyD88 independent immune signaling pathway mediated by phosphorylated IRF-3 for IFN-β response MyD88 negatively influences IFN-β response by sequestering IRF-3 or IRF-7 was proposed and MyD88 has been shown to interact with IRF3 and IRF7 through its TIR domain. In line with this, we next examined whether MyD88 inhibitor 4210 treatment would prevent its' association with IRF3/IRF7 and allow more phosphorylation of IRF3 in TLR3-dependent manner. Our earlier data showed that treatment of 4210 increased phosphorylation of IRF3 when stimulation with poly I: C (FIG. 12). To further confirm that MyD88 associate with IRF3/IRF7, we next examined for association of MyD88 and IRF3/IRF7 by co-transfection and co-immunoprecipitation experiements. HA-tagged IRF3 or IRF7 and Flag-tagged MyD88 plasmids were used for co-transfection of HEK293-TLR3 and co-immunoprecipitated from cell lysates using HA-conjugated agarose bead.

Figure 14A:
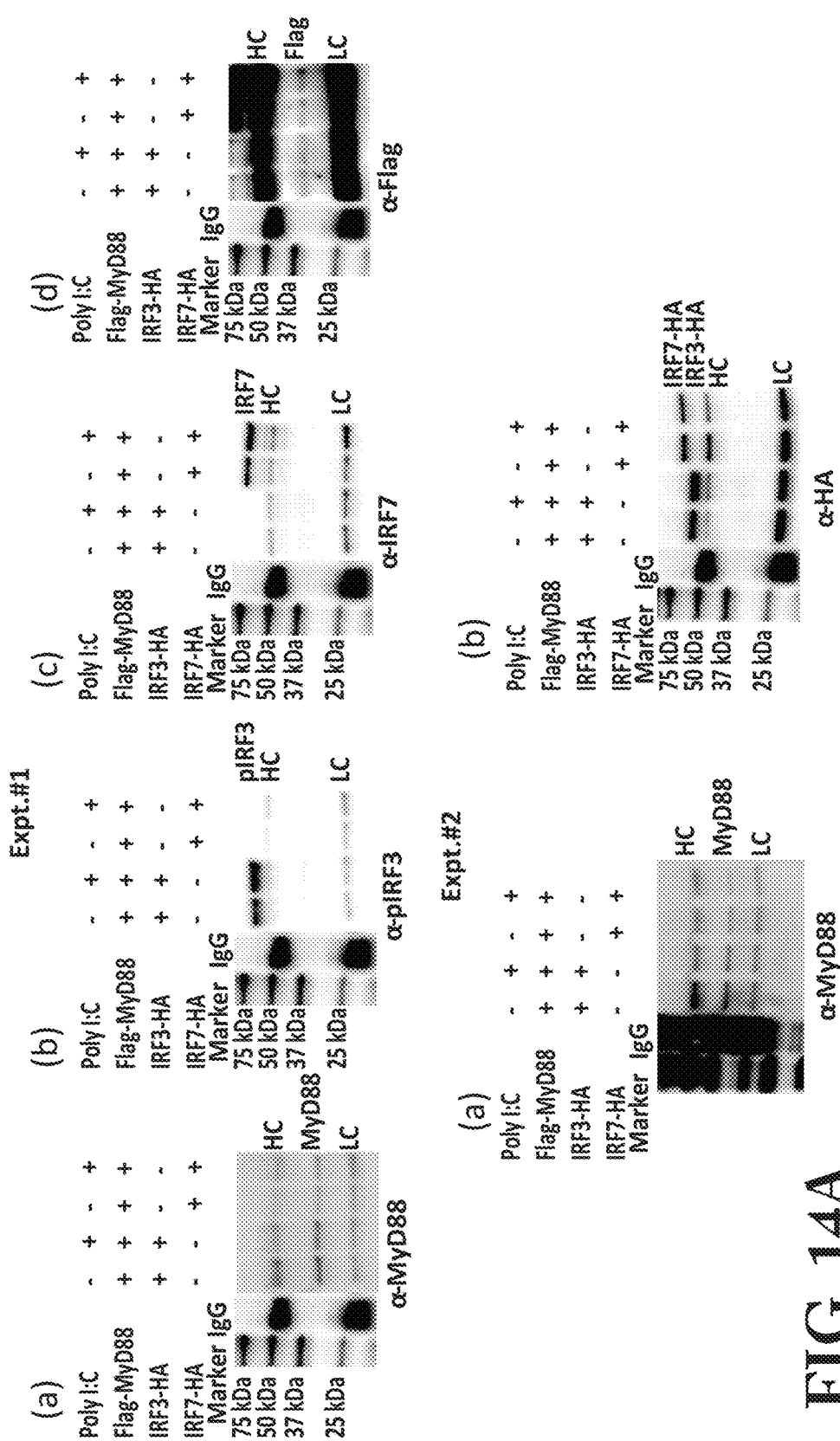
FIG. 14A is a series of graphs showing experiment #1 and experiment #2 relating to the association of MyD88 and IRF3/IRF7 upon co-transfection of HEK-TLR3 cells with Flag-MyD88/IRF-HA plasmids and stimulated with poly I:C, immune-precipitation of cell lysates IP by HA-Agarose and immunoblot analysis.
Figure 14B:
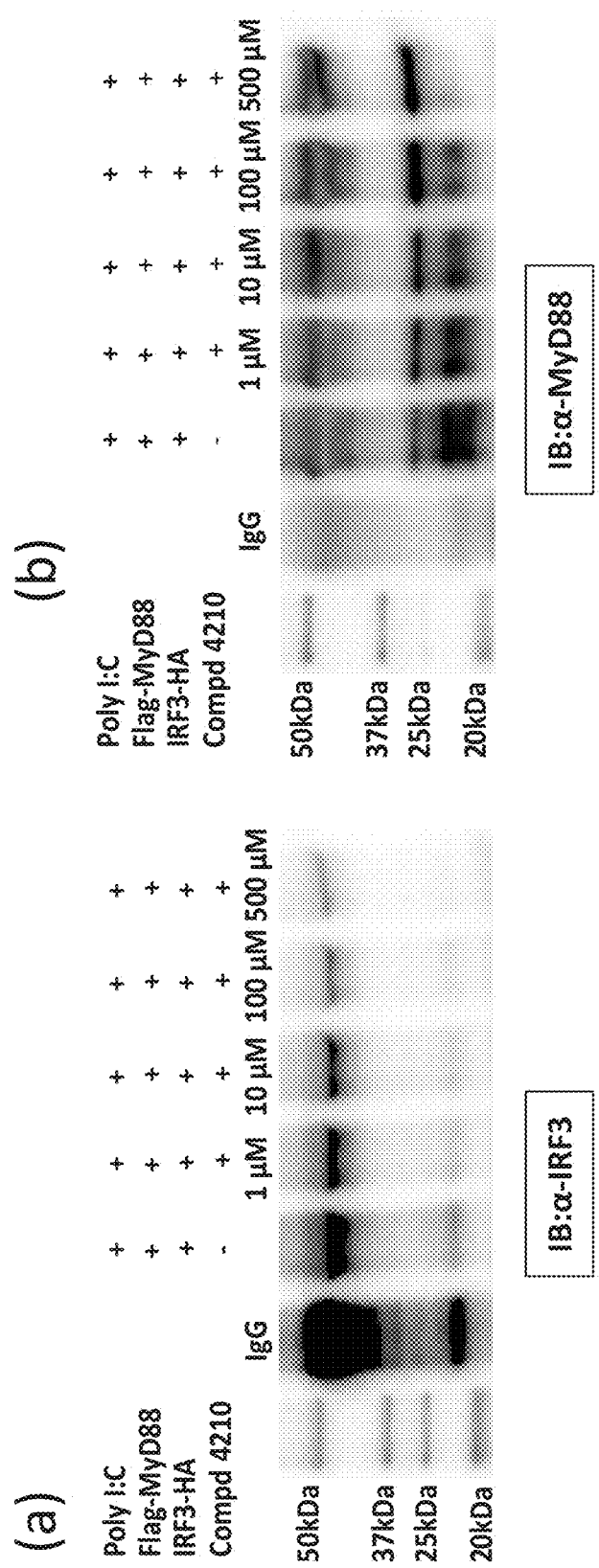
FIG. 14B is digital photograph of Inhibition of MyD88 and IRF3 interaction in the presence of compound 4210 in HEK-TLR3 cells co-transfected with Flag-MyD88 and IRF3-HA and immune-precipitation and immune-blot analysis.

After co-immunoprecipitation, followed by SDS-PAGE and immunoblot anaylasis with anti-MyD88 antibody, the 31 kDa MyD88 protein was detected (FIG. 14A, Exp#1(a)). After striping, the gel was reprobed with anti-pIRF3 as well as ant-IRF7 antibody and anti-HA antibody demonstrated the presence of IRF3 and IRF7 band suggesting an association of MyD88 with IRF3 and IRF7 (FIG. 14A, Expt #1 (b-d)). In a repeated experiment the results were confirmed (FIG. 14A, expt#2, (a) and (b)). In addition co-immunoprecipitation and immunoblotting experiment, we also performed mass spectrometry analysis of the MyD88-IRF immune-complex after HEK293 TLR3 cells over-expressing HA-tagged IRF3 or IRF7 following stimulation with poly I:C separated by SDS-PAGE, cutting the band for identifying IRF3 peptide by LC-MS. The results clearly demonstrated the identity of IRF3 that was pulled down by Flag antibody of MyD88 in complex with IRF3 (data not shown). These results suggest that MyD88 associate with IRF3 as well as IRF7. To further confirm that in the presence of MyD88 inhibitor compound 4210, the association MyD88 to IRF3 was inhibited, we performed similar co-transfection and co-immunoprecipitation experiment using Flag antibody to pull down complex, followed by SDS-PAGE and probed with anti-IRF. The results shown in FIG. 14B showed a dose dependent decrease of IRF3 band with high concentration of compound 4210 (FIG. 14B(a). To further confirm that the presence of MyD88, the gel was striped and reprobed with anti-MyD88 antibody. The 31 kDa MyD88 protein was detected and more accumulation of MyD88 was detected with higher concentration of 4210 (FIG. 14B(b)). The results suggest that in the presence of 4210, the unassociated MyD88 was pulled down by the Flag antibody in a dose dependent manner as shown in gel FIG. 14B (a,b). These results in agreement with previous report indicate that during poly I:C stimulation MyD88 associate with IRF3/IRF7 and 4210 disrupt this association.

Figure 15:
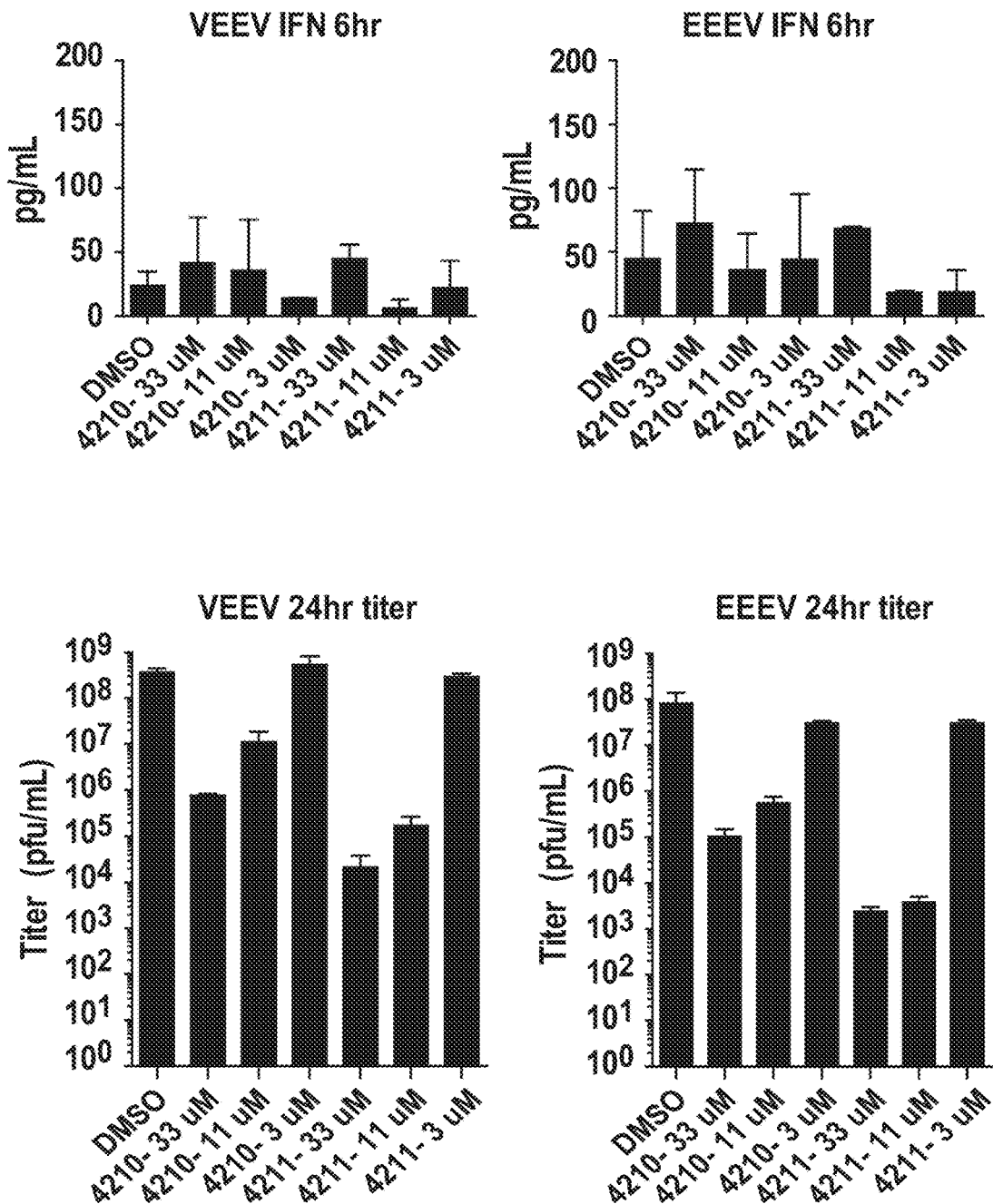
FIG. 15 is a series of graphs showing antiviral activity of compound 4210 and analog 4211 against VEEV and EEEV where virus replication correlates with IFN-β production.

Inhibition of VEEV and EEEV Replication in the Presence of 4210 in Infected Vero Cells, and U87 Cells To test further that MyD88 negatively interfere antiviral IFN-β response and inhibition of MyD88 would allow IFN-β mediated resistant to viral replication, we used VEEV and EEEV infection of human U87 and examined virus replication in a virus plaque reduction assay and also measured IFN-β in culture supernatant. Our results revealed that treatment of 4210 and 4211 at concentration 33 μM and 11 μM reduced VEEV and EEEV replication by 3-4 logs compared to compound untreated cells. Importantly reduction in virus replication correlated with up regulation of IFN-β (FIG. 15). Reduction in replication of VEEV and EEEV after infection of U87 and Vero cells were also confirmed by ELISA based assay detecting lack of viral E2 protein expression (data not shown). These results were also further confirmed by measuring the cell viability assay using cell titre-Glo assay (data not shown). These results demonstrate that inhibition of MyD88 by a small molecule inhibitor compound 4210 led to increased production IFN-β likely through IRF3-mediated immune signaling.

Figure 16:
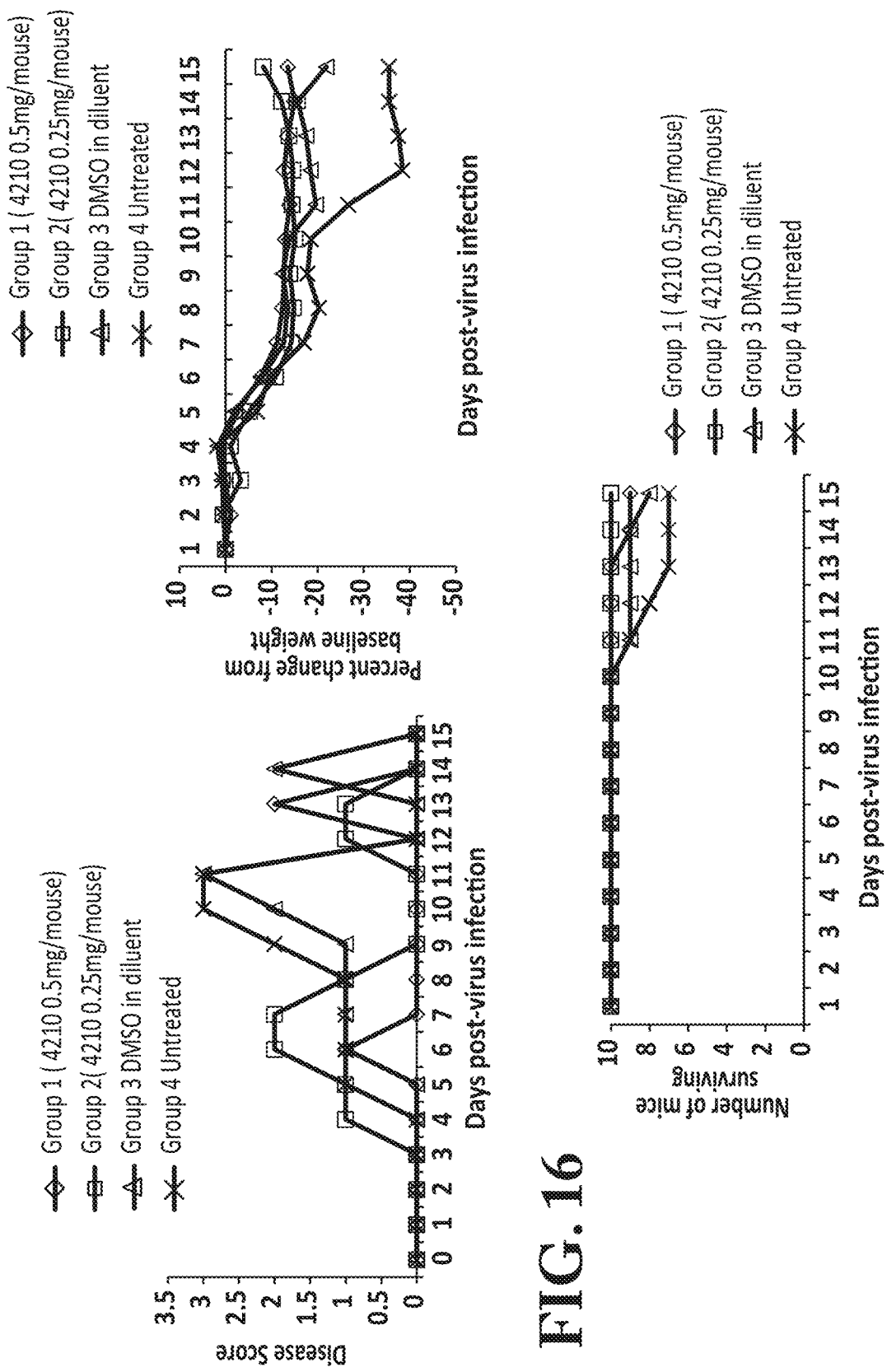
FIG. 16 is a series of graphs showing therapeutic efficacy of compound 4210 against VEEV infection in mice.
Figure 17:
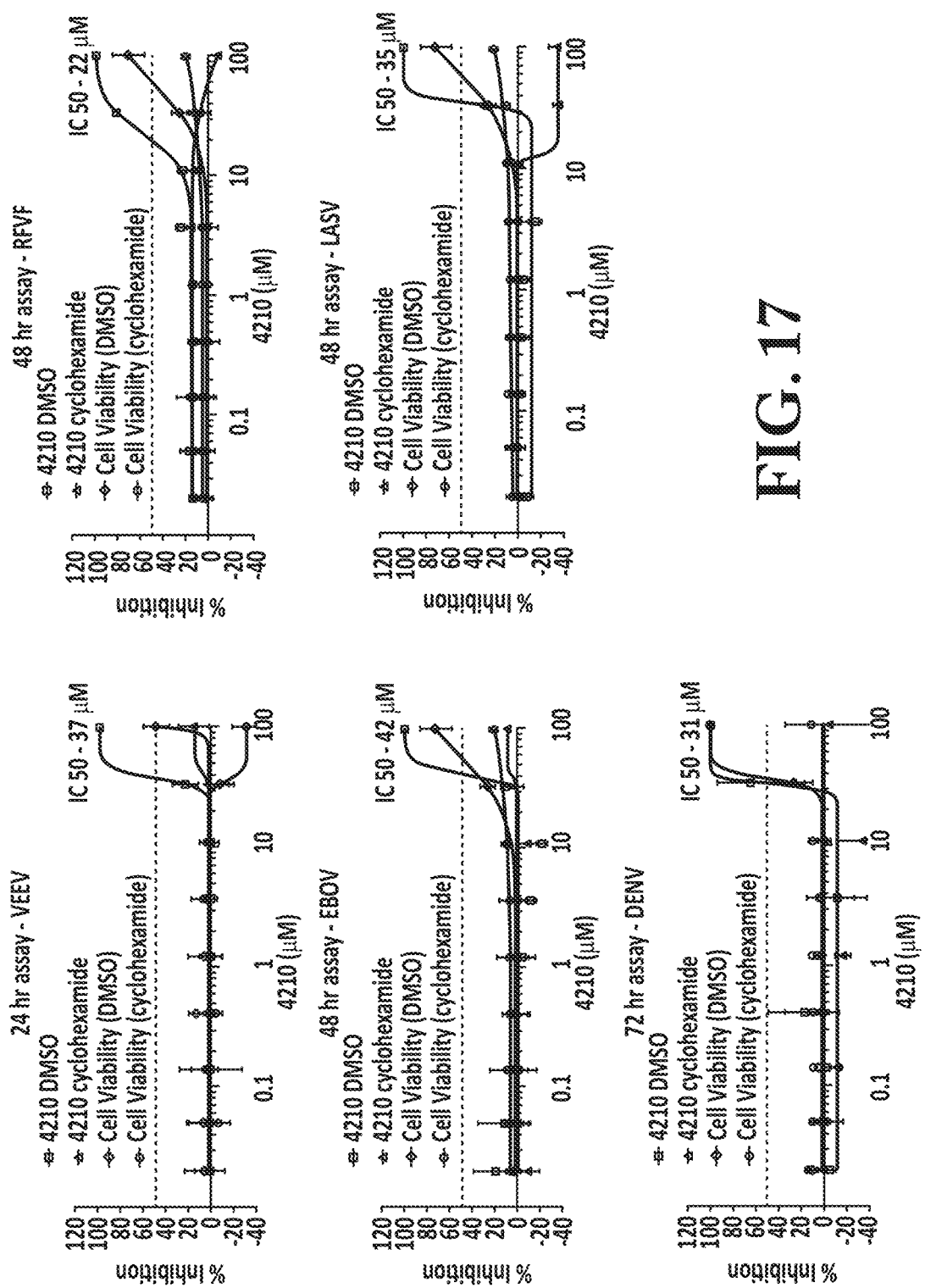
FIG. 17 is a graph showing anti-viral activity $IC_{50}$ values of 4210 against VEEV, RFVF, EBOV, LASA and DENV.
Figure 18:
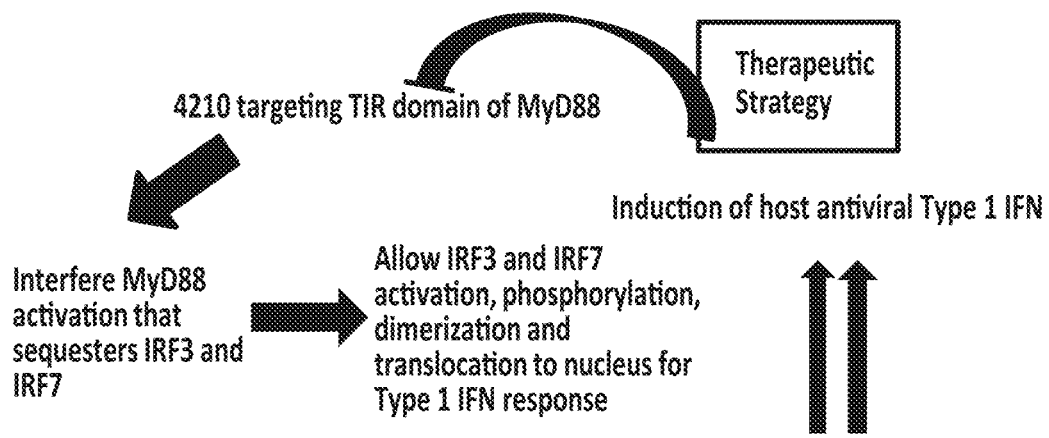
FIG. 18 is a flow chart showing a possible mechanism of anti-viral activity of compound 4210.

In Vivo Therapeutic Efficacy of Compound 4210 in a Lethal VEEV TC-83 Infection of C3H/HeN Mice Neuro-virulence of new world alphaviruses (EEEV, WEEV and VEEV) infections of central nervous systems results in pathogenesis and death of neural cells. C3H/HeN mice have been used extensively to study alphaviruses. Following infection, mice display human like disease with progression from infection of the lymphoid tissues and ultimate destruction of CNS tissues. Clinical symptoms in mice include: lethargy, huddling, dehydration, weight loss, tremors, and paralysis or paresis with a minority of animals developing seizures. Intranasal administration of TC83 in C3H/HeN mice closely mimics virulent VEEV encephalitis in murine models and has been used as a model to evaluate antivirals for alphavirus infection (Julander J. G. et al., 2008).To test that MyD88 inhibition following post-exposure treatment by a MyD88 inhibitor 4210 would lead to reduced virus replication by up regulating IFN-β production, and protect against VEEV infection, we used C3H/HeN mouse model VEEV infection. 2 h prior to intranasal inoculation of vaccine strain of VEEV (TC-83) ($1 \times 10^5$ pfu) mice were pretreated with 4210 (0.5 mg/mouse or 0.25 mg/mouse) or with diluent or without treatment. Compound was administered two times per day by i.p. from D0 to D4. On D0, dosing started at 8 hours post virus challenge. All animals were weighed and observed for clinical signs twice daily from D0 to D14. The median time-to-death for the group challenged with VEEV was 9-10 days. The treatment of 4210 significantly prevented weight loss, less clinical diseases score and increased survival of mice as compared to without treatment (FIG. 16). The experiment is underway with higher virus inoculum (10LD50; 2×107 pfu) and virulent strain of VEEV (Trinidad virus).

Reduction in Replication of Rift Valley Fever Virus (RFVF), Dengue Virus (DENY), Lasa Fever Virus (LASV) and Ebola Virus (EBOV) in Infected Vero Cells in the Presence of 4210.

In general, to mount host directed antiviral immunity, IFN is one of the most crucial molecules in the innate immune response and acts as the primary switch for initiating antiviral immunity in vertebrates. Due to the significance of IFN in the host cells to restrict viral infections and as MyD88 is involved negatively in regulating or controlling the host anti-viral immunity, we evaluated whether it happens with other viral infections besides VEEV or EEEV infections. For this we examined whether 4210 treatment would increase antiviral immunity as tested with VEEV and EEEV and will reduce the viral replication such as RFVF, DENY, LASV and EBOV, infection. We tested in ELISA based assay of virus protein expression in infected cells and cell viability in the presence of 4210. Our results demonstrated that similar to $IC_{50}$ values VEEV and EEEV, ex vivo infection of Vero cells in the presence of 4210 reduced replication of Rift valley fever virus ($IC_{50}$ 22 μM), Lassa virus ($IC_{50}$ 35 μM), dengue virus ($IC_{50}$ 31 μM) and Ebola virus (42 μM). These results suggest that 4210 treatment may induce Type 1I IFN with other viral infection and limit virus replication.

Discussion

In this study we have shown that during viral infections intracellular immune signaling adaptor protein MyD88 is up regulated and this up regulation inhibited antiviral IFN-β and RANTES production. Likewise our results showed that treatment of MyD88 inhibitor 4210 in multiple cells with a virus like infection (poly I: C stimulation) increased antiviral IFN-β and RANTES production. In addition our data also demonstrated that an increase in antiviral IFN-β production was due to increase in IRF-3 phosphorylation. The increased production of these antiviral IFN-β and RANTES correlated with reduction of alpha virus yield in infected cells and increased in cell viability. Importantly, post exposure treatment with a MyD88 inhibitor after lethal VEEV infection, protected mice from death. These results provide evidence that intracellular adaptor protein MyD88 plays a negative role during alpha virus infections, and inhibition of MyD88 improved host directed adaptation to antiviral immunity. Besides anti alpha viral activity of MyD88 inhibitor 4210, spectrum of antiviral activity against including non-enveloped DNA virus, both positive and negative strand RNA virus was observed. These results are in agreement with earlier reports which suggested that during viral infections MyD88 is up regulated and that up regulation negatively influenced impairment of antiviral immunity by curtailing type 1 IFN-β production. While all alpha viruses demonstrate sensitivity to type I IFNs, nonetheless, host induction of type I IFNs appears to be inadequate to clear the infection.

Thus, our study provides for the first time delineate an underlying mechanism of inadequate antiviral immunity where IFN-I induction is subject to negative regulation influenced by MyD88.

One of the goals in virology research for developing effective antiviral therapeutics is to stimulate type I IFN because IFNs have long been recognized as essential components of the innate immune response to viral infections (Baron, S. et al. 1991.JAMA 266:1375-1383), and specifically, IFN-α/β are known to be important determinant in protecting viral infections including alpha viral diseases (Grieder, F. B. and S. N. Vogel 1999, Virology 257:106-118). Throughout the course of viral infection type IIFN constantly monitors the virus through immune battle. Upon initial infection, if the antiviral and immune-stimulatory effects of IFN-I (direct antiviral effects) predominates, then it will allow the host's ability to take over the positive effects of IFN-I and subsequently other interferon stimulating genes (ISG) to clear the infection. In this regard, recently much attention has been focused on the induction and function of the IFN-α/β system that are activated by TLRs and (RIG-I and MDA-5) like receptors that are affected by intracellular TLR adaptors (Siednoko J G et al.2010, 2011). The receptor engaged immune signaling pathways leading to antiviral type I IFN response are reported to be tightly regulated by the host are becoming increasingly understood. A number of recent studies highlight the role of TLR adaptors namely intracellular MyD88 and MyD88-adaptor-like (MAL) in the negative regulation of viral immunity (Siednienko J et al., 2010, 2011). Importantly, it has been demonstrated that while MyD88 is up regulated during some viral infections such as coxsackie virus 3 infections, alpha virus infections and TIR domain containing MyD88 is significantly up regulated (Fuse k, et al., 2005, Sharma A et al., 2009). Furthermore, it is now known that type I IFN-β gene induction was significantly enhanced in MyD88 and Mal deficient cells following poly I: C stimulation and following treatment of cells with Mal-inhibitory peptide (Siednienko J et al., 2010, 2011). Also, absence of MyD88 results in enhanced TLR-dependent phosphorylation of IRF3 and increased IFN-β and RANTES production. Thus, MyD88/ Mal has the ability to differentially regulate various signals emanating from TLRs and upon sensing viral infections, MyD88/Mal contributes to inhibitory host immune response due to their ability to sequester IRF3/IRF7 away from TLR3/ (TIR) domain-containing adaptor-inducing IFN-β (TRIF) and/or RIG-I/MDA-5 receptor mediated signaling. By doing so, MyD88 or Mal impairs host directed IFN-induction which is critical to clear the infection. Recently it has been suggested that because innate immune cells express various types of the receptors, distinct combinations of signaling pathways are activated in response to a given pathogen which may elicits antagonism between the individual pathways, where attenuation of a signaling pathway(s) by others may results in the outcome of the immune response (Negishi H et al., PNAS 2013). This event sometimes may favor the pathogens to avoid host directed immune response. In line with this view, our results demonstrated an increased induction of antiviral IFN-β in multiple cells with poly I: C stimulation in the presence of MyD88 inhibitor correlated with increased phosphorylation of IRF3. Given that despite type I IFN sensitivity of all alpha viruses during VEEV infection expression of type 1 IFN response appears to be inadequate to clear the infection (Simmons J. D et al., 2009, J. Virol. 83:10571-10581). In this study, our results provide evidence that negative effect of MyD88 on type 1 IFN induction may be one of the immune evasion strategy of VEEV that are utilized for dissemination for causing diseases. Recent report by Zhou, Zhi-xia et al., 2014 (PLoSOne 9(11):e112918) demonstrated that antiviral immune response of Poly I:C requires TLR3 and MDA5 and is negatively regulated by MyD88 and treatment of MyD88 inhibitor increased type I IFN and other ISG in Japanese Flounder (paralichthys olivaceus) infected with megalocytivirus. In agreement with these reports, our results demonstrated that annulment of the negative effect of MyD88 which sequesters IRF-3 and thereby restricts the IRF-3 mediated IFN signaling, drove the host's full blown adaptation to antiviral response. Inactivation MyD88 through TIR domain binding inhibitor, allowed not to interact and sequestering IRF3/IRF7 and restored fully TLR3-TRIF-IRF3-mediated immune signaling and refurbished antiviral IFN-β to achieve hosts' full pledged anti-viral immunity. Our results also revealed that in addition to IFN-β induction it also induced antiviral RANTES. These results are in agreement with earlier speculation that MyD88 sequester IRF3/IRF7 through TIR domain interaction and impairs antiviral immunity. Thus, MyD88 negatively influence IRF3/7 (TLR3-TRIF-IRF-IFN-β) signaling pathway and a possible mechanism of type I IFN impairment.

To summarize, it appears that induction of innate immunity during viral infections predominantly depends on the balance of the signal contributed by MyD88.

Induction of Innate immunity and it's regulation is distinctly a combination of signaling pathways which may co-operate or interfere with one another in a ways that might be beneficial or antagonistic to shape the host immunity (7, Negishi, H et al., 2013, Beneficial innate signaling interference for antimicrobial responses by a toll-like receptor-mediated enhancement of the MKP-IRF3 axis. Proc. Natl. Aca. Sci. 110, 19884-19889). Cell-intrinsic innate immune responses are essential for pathogen control and cell survival after infection (Daffis, S et al., 2007, Plos pathog. 3:1106; Detje, C N et al. 2009; J. Immunol. 182:2297-2304; Griffin D E 2003 Nat. Rev. immunol. 3:493-502) and an effective response in neurons may be crucial to prevent irreversible loss of critical CNS neurons following this neurotropic virus infection. To test that MyD88 inhibition by 4210 and its isomer 4211 would lead to reduction in virus replication by up regulating IFN-β production, we infected U87 cells and Vero cells with VEEV and EEEV and examined virus replication by plaque reduction assay.

One of the goals in virology research for developing effective antiviral therapeutics is to identify viral and host factors involved in infection. In viral infections generally type 1 IFN-α/β system are responsible for inducing transcription of a large group of genes which play a role in host resistance as well as activating key components of innate and adaptive immune systems. However, IFN-I induction is subject to negative regulation by both viral and cellular factors. Recently it was reported that in MyD88$^{-/-}$ mice administered Ebola virus-like particles (eVLP), a candidate vaccine for Ebola virus (EBOV) infection,a significant increase of Pan IFN-α, IFN-β, IRF1 and IRF7 along with interferon stimulated gene(s) (ISG) were expressed in MyD88$^{-/-}$ dendritic cells (DCs) than those of MyD88$^{+/+}$ DCs (5). Our studies have provided evidence that a strong initial IFN responses which function as the critical rheostat in an immunologic surveillance system that measures the duration and magnitude of virus replication (i.e. whether the host or pathogen is winning the battle). Our data suggest that MyD88 inhibition potentially enhancing IFN-I signaling by taking over the host strategy through annulment of the negative factor contributed by MyD88 and influencing the host antiviral immunity to therapeutically resolve the infections. Thus, our study provides a novel approach of host directed antiviral therapy. Importantly, targeting the host may result in therapies with a broader range than traditional antivirals.

IFN is a key regulator of the innate immune response and has been used for treating infectious diseases (Keam S J and Cvetkovic R S (2008) Drugs 68::1273-1317; Bergman S J et al. 2011) Infect Dis Clin North Am 25:819-834). Any molecule with the ability to modulate the innate immune system by promoting the synthesis of IFN would have potentially dual application as both an antiviral and a vaccine adjuvant. Compound 4210 treatment induced IFN with Poly I: C as well as virus infection and increased expression co-stimulatory molecules such as CD86 and CD80 in U937 cells, which is a secondary effect to IFN production. Thus, it would be interesting to examine whether 4210 has an adjuvant effect.

Some important features of the invention include the following points: Virus or virus-like infections (poly I: C stimulation) are known to up regulate MyD88. Up regulation of MyD88 impairs anti-viral type I IFN induction and antiviral immunity. Our results demonstrate that treatment of a MyD88 inhibitor (compound 4210) increased IFN-β and RANTES production concomitant with IRF3 phosphorylation. MyD88 inhibition (i.e., the annulment of negative effect of MyD88 by compound 4210) disables IRF3/IRF7 sequestering capacity of MyD88, thus, allows more IRF-phosphorylation and an increase in antiviral type 1 IFN and RANTES response.

Therefore, MyD88 inhibition up regulates anti-viral immune response, and reveals a novel approach of host directed anti-viral therapy.

The compound 4210 is stable at room temperature for two years. It can be administered intraperitoneally. For administration, it is dissolved in DMSO, then diluted to PBS and 5% BSA and injected only as described above (100 microliter volume).

Accordingly, although embodiments of the present invention have been shown and described, it would be appreciated by those skilled in the art that changes may be made in these embodiments without departing from the principles and spirit of the invention, the scope of which is defined in the claims and their equivalents.

Disclosures

Research was conducted under an IACUC approved protocol in compliance with the Animal Welfare Act and other Federal statutes and regulations relating to animals and experiments involving animals and adhere to principles stated in the *Guide for the Care and Use of Laboratory Animals,* National Research Council, 1996. The facility where this research was conducted is fully accredited by the Association for Assessment and Accreditation of Laboratory Animal Care International. Peripheral blood mononuclear cells used in this study were obtained from healthy donors with written consents, in accordance with guidelines of the human use committee (HUC) and institutional (USAMRIID) review board-approved research donor protocol FY 05-05.

What is claimed is:
1. A synthetic small molecule that inhibits myeloid differentiation primary response protein 88 (MyD88) comprising: $C_{44}H_{64}N_4O_4$, wherein said synthetic small molecule has the following chemical structure:

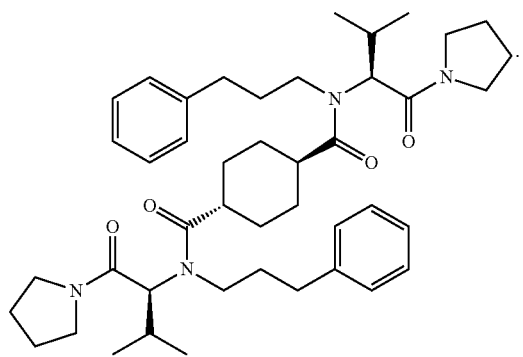 [SMILES: CC(C)[C@@H](C(=O)N1CCCC1)N(CCCc1ccccc1)C(=O)[C@H]1CC[C@H](C(=O)N(CCCc2ccccc2)[C@H](C(=O)N2CCCC2)C(C)C)CC1]

2. A method of treating viral infections comprising administering to a subject a therapeutically effective amount of the synthetic small molecule of claim 1.

3. The method of claim 2, wherein said viral infections include encephalitic alphavirus infections comprising one or more of Venezuelan Equine Encephalitic Virus (VEEV), Eastern Equine Encephalitic Virus (EEEV) and Western Equine Encephalitic Virus (WEEV).

4. The method of claim 2, wherein said subject is a mammal.

5. A method of increasing IFN-β and RANTES production concomitant with IRF3 phosphorylation comprising: administering the synthetic small molecule of claim 1.

6. A method of inhibiting MyD88 and up regulating an anti-viral immune response in a host comprising administering a therapeutically effective amount of the synthetic small molecule of claim 1.

7. A method of treating bacterial toxin exposure from bacteria following infections or exposure to enterotoxins comprising administering to a subject a therapeutically effective amount of the synthetic small molecule of claim 1.

8. The method of claim 7, wherein said bacteria include Gram positive bacterial infections caused by *staphylococcal* enterotoxin B (SEB).

9. The method of claim 7, wherein said bacteria include Gram negative bacterial infections caused by *Francisella tularensis, Burkholderia pseudomallei, E. coli* and *Burkholderia mallei.*

10. The method of claim 7, wherein said subject is a mammal.

11. A method of treating toxic shock syndrome caused by staphylococcal enterotoxin B (SEB) comprising administering a therapeutically effective amount of the synthetic small molecule of claim 1.

12. A method of treating septic shock caused by *Francisella tularensis, Burkholderia pseudomallei* and *Burkholderia mallei* comprising administering a therapeutically effective amount of the synthetic small molecule of claim 1.

13. A method of treating endo- and entero-toxins comprising administering a therapeutically effective amount of the synthetic small molecule of claim 1 as an antidote of inflammatory response.

14. A method of inhibiting pro-inflammatory cytokine production of IL-1β, IL-6, IL-2, TNF-α and INF-γ in primary human cells comprising:
administering synthetic small molecule of claim 1 to said primary human cells.

15. A method of improving a IRF3/7 (TLR3-TRIF-IRF-IFN-β) signaling in cells comprising administering the synthetic small molecule of claim 1 to said cells.

16. A host directed anti-viral therapy comprising: administering the small molecule of claim 1 to a host subject.

17. A method of treating viral infections comprising administering to a subject a therapeutically effective amount of a synthetic small molecule that inhibits myeloid differentiation primary response 88 (MyD88) comprising: $C_{44}H_{64}N_4O_4$, wherein said synthetic small molecule has the following chemical structure:

18. The method of claim 17, wherein said viral infections include encephalitic alphavirus infections comprising one or more of Venezuelan Equine Encephalitic Virus (VEEV), Eastern Equine Encephalitic Virus (EEEV) and Western Equine Encephalitic Virus (WEEV).

19. A method of treating bacterial toxin exposure from bacteria following infections or exposure to enterotoxins comprising administering to a subject a therapeutically effective amount of a synthetic small molecule that inhibits myeloid differentiation primary response protein 88 (MyD88) comprising: $C_{44}H_{64}N_4O_4$, wherein said synthetic small molecule has the following chemical structure:

20. The method of claim 19, wherein said bacteria include Gram positive bacterial infections caused by staphylococcal enterotoxin B (SEB) and Gram negative bacterial infections caused by *Francisella tularensis, Burkholderia pseudomallei, E. coli* and *Burkholderia mallei*.

* * * * *